US012295815B2

United States Patent
Carrillo Ojeda et al.

(10) Patent No.: US 12,295,815 B2
(45) Date of Patent: May 13, 2025

(54) METHODS OF MANUFACTURING ZONED WEBS

(71) Applicant: Kimberly-Clark Worldwide, Inc., Neenah, WI (US)

(72) Inventors: Antonio J. Carrillo Ojeda, Appleton, WI (US); Davis Dang H. Nhan, Menasha, WI (US); Dwayne J-K Jackson, Atlanta, GA (US); Juha P. Kemppinen, Cumming, GA (US); Mark M. Mleziva, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 18/274,734

(22) PCT Filed: Jan. 29, 2021

(86) PCT No.: PCT/US2021/015735
§ 371 (c)(1),
(2) Date: Jul. 28, 2023

(87) PCT Pub. No.: WO2022/164443
PCT Pub. Date: Aug. 4, 2022

(65) Prior Publication Data
US 2024/0099899 A1    Mar. 28, 2024

(51) Int. Cl.
*D04H 1/495* (2012.01)
*A61F 13/15* (2006.01)
*C08J 5/00* (2006.01)

(52) U.S. Cl.
CPC .......... *A61F 13/15666* (2013.01); *C08J 5/00* (2013.01); *D04H 1/495* (2013.01); *C08J 2321/00* (2013.01); *D10B 2509/026* (2013.01)

(58) Field of Classification Search
CPC ........ D04H 1/498; D04H 1/495; D04H 1/492; D04H 1/49; A61F 13/513; A61F 13/15723; A61F 13/532; A61F 13/535; B32B 5/067
See application file for complete search history.

(56) References Cited

U.S. PATENT DOCUMENTS

| 362,618 A | 5/1887 | Gordon |
| 3,338,992 A | 8/1967 | Allison |

(Continued)

FOREIGN PATENT DOCUMENTS

| CN | 104939977 A | 9/2015 |
| JP | 2003247156 A | 9/2003 |

(Continued)

OTHER PUBLICATIONS

New Scientist, "Diaper tech: inspired by babies", Jan. 25, 2017, https://www.newscientist.com/article/mg23331101-000-diaper-tech/.

*Primary Examiner* — Jillian K Pierorazio
(74) *Attorney, Agent, or Firm* — KIMBERLY-CLARK WORLDWIDE, INC.

(57) ABSTRACT

A method of manufacturing zoned webs can include providing a substrate and transferring the substrate in a machine direction. The method can include modifying the substrate to include a plurality of lanes to provide a modified substrate. The plurality of lanes can include a first lane and a second lane. The first lane can include a first zone and a second zone. The first zone can include an open area greater than an open area of the second zone. The second lane can include a third zone and a fourth zone. The third zone can include an open area greater than an open area of the fourth zone. The first lane and the second lane can be formed such that the first zone in the first lane is staggered in the machine direction from the third zone in the second lane. The method (Continued)

can also include slitting the modified substrate between adjacent lanes in the plurality of lanes to provide zoned webs.

16 Claims, 8 Drawing Sheets

(56) References Cited

U.S. PATENT DOCUMENTS

| | | | |
|---|---|---|---|
| 3,341,394 A | 9/1967 | Allison | |
| 3,485,706 A * | 12/1969 | Evans | D04H 1/495 |
| | | | 162/204 |
| 3,502,538 A | 3/1970 | Petersen | |
| 3,502,763 A | 3/1970 | Hartmann | |
| 3,542,615 A | 11/1970 | Dobo et al. | |
| 3,802,817 A | 4/1974 | Matsuki et al. | |
| 4,340,563 A | 7/1982 | Appel et al. | |
| 4,939,016 A | 7/1990 | Radwanski et al. | |
| 4,959,531 A | 9/1990 | Marino | |
| 4,970,104 A | 11/1990 | Radwanski | |
| 5,098,764 A * | 3/1992 | Bassett | D04H 1/495 |
| | | | 28/104 |
| 5,895,623 A * | 4/1999 | Trokhan | D04H 1/64 |
| | | | 28/106 |
| 6,452,063 B1 | 9/2002 | Curro et al. | |
| 7,175,613 B2 | 2/2007 | Sugiyama et al. | |
| 8,022,267 B2 | 9/2011 | Hellström et al. | |
| 8,057,879 B2 | 11/2011 | Middlesworth et al. | |
| 8,968,516 B2 | 3/2015 | Super et al. | |
| 9,445,951 B2 | 9/2016 | Moberg-Alehammar et al. | |
| 10,271,999 B2 | 4/2019 | Arora et al. | |
| 2006/0005919 A1 * | 1/2006 | Schewe | A61F 13/15658 |
| | | | 156/276 |
| 2008/0281286 A1 * | 11/2008 | Petersen | A61F 13/15593 |
| | | | 604/385.24 |
| 2009/0005752 A1 | 1/2009 | Suzuki et al. | |
| 2009/0123707 A1 * | 5/2009 | Skoog | D04H 1/498 |
| | | | 264/103 |
| 2013/0101805 A1 * | 4/2013 | Altshuler | B32B 3/30 |
| | | | 264/109 |
| 2015/0282997 A1 | 10/2015 | Arizti et al. | |
| 2015/0313766 A1 * | 11/2015 | Miao | A61F 13/5125 |
| | | | 604/385.101 |
| 2017/0027768 A1 * | 2/2017 | Stabelfeldt | A61F 13/491 |
| 2017/0233909 A1 * | 8/2017 | Wright | D04H 1/4374 |
| | | | 428/172 |
| 2017/0266941 A1 | 9/2017 | Eimann et al. | |
| 2018/0056624 A1 * | 3/2018 | Yang | B32B 27/12 |
| 2018/0105965 A1 * | 4/2018 | Pourdeyhimi | D04H 1/492 |
| 2019/0270224 A1 * | 9/2019 | Thomas | A61F 13/15731 |
| 2019/0358679 A1 * | 11/2019 | Possell | B32B 5/024 |
| 2020/0378044 A1 * | 12/2020 | Beitz | D04H 1/495 |
| 2021/0214869 A1 * | 7/2021 | Fujita | D06B 23/042 |

FOREIGN PATENT DOCUMENTS

| | | |
|---|---|---|
| JP | 2007190315 A | 8/2007 |
| JP | 2009050621 A | 3/2009 |
| JP | 2011021310 A | 2/2011 |
| WO | 2001072251 A1 | 10/2001 |
| WO | WO-2020112956 A1 * | 6/2020 ....... A61F 13/15731 |

* cited by examiner

METHODS OF MANUFACTURING ZONED WEBS

TECHNICAL FIELD

The present disclosure relates to method of manufacturing webs. More specifically, the present disclosure relates to methods of manufacturing zoned nonwoven webs.

BACKGROUND OF THE DISCLOSURE

Fibrous nonwoven web materials are in wide use in a number of applications including but not limited to absorbent structures and wiping products, many of which are disposable. In particular, such materials are commonly used in personal care absorbent articles such as diapers, diaper pants, training pants, feminine hygiene products, adult incontinence products, bandages, and wiping products such as baby and adult wet wipes. They are also commonly used in cleaning products such as wet and dry disposable wipes which may be treated with cleaning and other compounds which are designed to be used by hand or in conjunction with cleaning devices such as mops. Yet a further application is with beauty aids such as cleansing and make-up removal pads and wipes.

In some of these applications, there may be a desire to have zoned features, in which different areas of a fibrous web provide different properties, particularly for different intended uses of the product. For example, it may be desired to have a diaper with a zoned fibrous web having a first area configured for intaking and managing urine, and a second area configured for intaking and managing feces.

Producing such zoned webs can provide difficulties due to the non-uniform properties of the web across different machine directional zones of the web. This is particularly relevant where a wider web is initially manufactured that includes multiple lanes of the zoned material. Differences in the physical characteristics of the web at various zones web can create significant web handling issues, including, but not limited to, curling, tracking, spooling, and web breaks. These issues can cause delays in manufacturing and/or increased costs for manufacturing such zoned webs.

As a result, there is a need for methods and apparatuses that provide for improved handling of zoned webs. There remains a need for minimizing curling and/or web breaks for webs that have machine directional zoned areas that provide non-uniform properties between zones and, in particular, for producing a plurality of zoned webs from a wider web that includes a plurality of lanes of zoned areas.

SUMMARY OF THE DISCLOSURE

In one embodiment, a method of manufacturing zoned webs is provided. The method can include providing a substrate. The method can also include transferring the substrate in a machine direction. The method can further include modifying the substrate to include a plurality of lanes to provide a modified substrate. The plurality of lanes can include a first lane and a second lane. The first lane can include a first zone and a second zone. The first zone can include an open area greater than an open area of the second zone. The second lane can include a third zone and a fourth zone. The third zone can include an open area greater than an open area of the fourth zone. The first lane and the second lane can be formed such that the first zone in the first lane is staggered in the machine direction from the third zone in the second lane. The method can also include transferring the modified substrate. The method can additionally include slitting the modified substrate between adjacent lanes in the plurality of lanes to provide zoned webs. The zoned webs can include a first zoned web including the first lane and a second zoned web including the second lane.

In another embodiment, another method of manufacturing zoned webs is provided. The method can include providing a nonwoven substrate. The method can also include transferring the substrate in a machine direction to a fluid entanglement apparatus. The fluid entanglement apparatus can include a pattern surface and a plurality of fluid entanglement jets. The pattern surface can include a plurality of pattern lanes. The plurality of pattern lanes can include a first pattern lane and a second pattern lane. The first pattern lane can include a first pattern zone and a second pattern zone. The first pattern zone can include a first plurality of projections. The second pattern lane can include a third pattern zone and a fourth pattern zone. The third pattern zone can include a third plurality of projections. The third pattern zone and the fourth pattern zone can be formed such that the first pattern zone in the first pattern lane is staggered in the machine direction from the third pattern zone in the second pattern lane. The method can also include fluid entangling the substrate with the fluid entanglement jets over the pattern surface to provide a modified substrate including a plurality of lanes including a first lane and a second lane. The method can further include transferring the modified substrate. Additionally, the method can include slitting the modified substrate between adjacent lanes in the plurality of lanes to provide zoned webs. The zoned webs can include a first zoned web including the first lane and a second zoned web including the second lane.

In yet another embodiment, a method of manufacturing zoned webs is provided. The method can include providing a substrate. The method can include transferring the substrate in a machine direction. The method can include modifying the substrate to include a plurality of lanes to provide a modified substrate. The plurality of lanes can include a first lane including a first zone and a second zone. The first zone can include a first substrate characteristic. The second zone can include a second substrate characteristic. The first substrate characteristic and the second substrate characteristic can provide different substrate handling characteristics between the first zone and the second zone. The plurality of lanes can also include a second lane including a third zone and a fourth zone. The third zone can include a third substrate characteristic. The fourth zone can include a fourth substrate characteristic. The third substrate characteristic and the fourth substrate characteristic can provide different substrate handling characteristics between the third zone and the fourth zone. The substrate can be modified such that the first lane and the second lane are configured such that the first zone in the first lane is staggered in the machine direction from the third zone in the second lane. The method can also include transferring the modified substrate. Additionally, the method can include slitting the modified substrate between adjacent lanes in the plurality of lanes to provide zoned webs. The zoned webs can include a first zoned web including the first lane and a second zoned web including the second lane.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
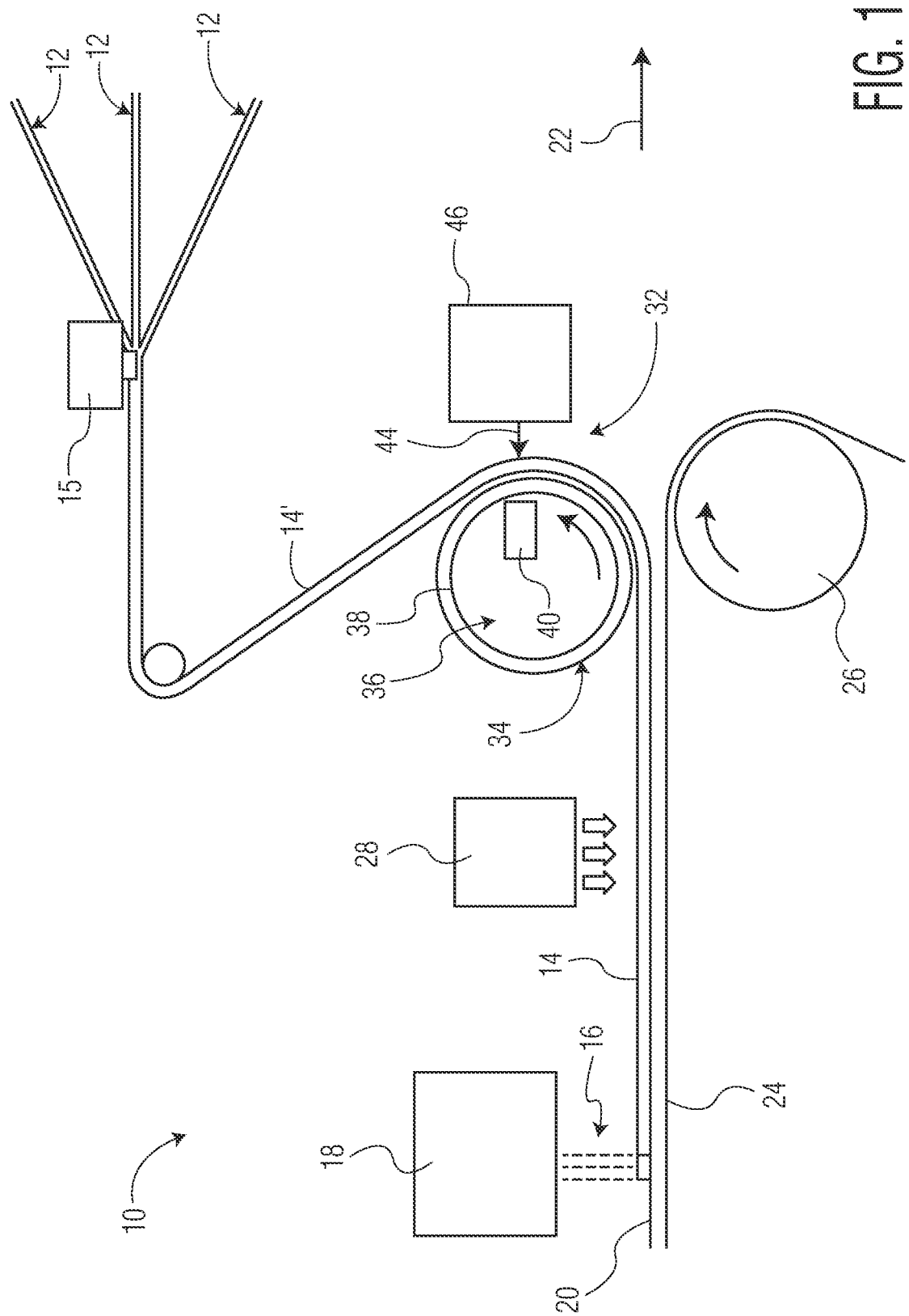
FIG. 1 is a schematic side view of an exemplary apparatus and method for manufacturing zoned webs according to the present invention.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards methods 10 for manufacturing zoned webs 12 and apparatuses that can employ such methods 10. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "fluid entangling" and "fluid-entangled" generally refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) is then directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, their fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

A method 10 for manufacturing zoned webs 12 is depicted in FIG. 1. As will be described herein, one exemplary method 10 for manufacturing zoned webs 12 can be include a fluid entanglement process, however, it can be appreciated that other techniques for modifying a substrate 14 in order to provide zoned webs 12 and are within the scope of the disclosure. As illustrated in FIG. 1, the method 10 can include providing a substrate 14. The substrate 14 can include a plurality of fibers. The substrate 14 can be formed from a variety of techniques of web forming, such as, but not limited to a wet-laying, a foam-laying, or a carding process. In a preferred embodiment as depicted in FIG. 1, the substrate 14 can be formed by a wet-laying process through a fiber and water slurry 16 being deposited from a drum 18 on a precursor forming surface 20. The precursor forming surface 20 as shown in FIG. 1 can be a precursor material, such as a spunbond web. However, it is contemplated that the fiber and water slurry 16 can be deposited directly on a belt, screen, or other surface that provides a precursory forming surface 20. The substrate 14 can be transferred in a machine direction by a belt 24 driven by a drive roll 26, or other transfer devices known by one of ordinary skill in the art. If the substrate 14 is formed through a wet-laying process, the substrate 14 can be dried through known techniques with a dryer 28.

Figure 2:
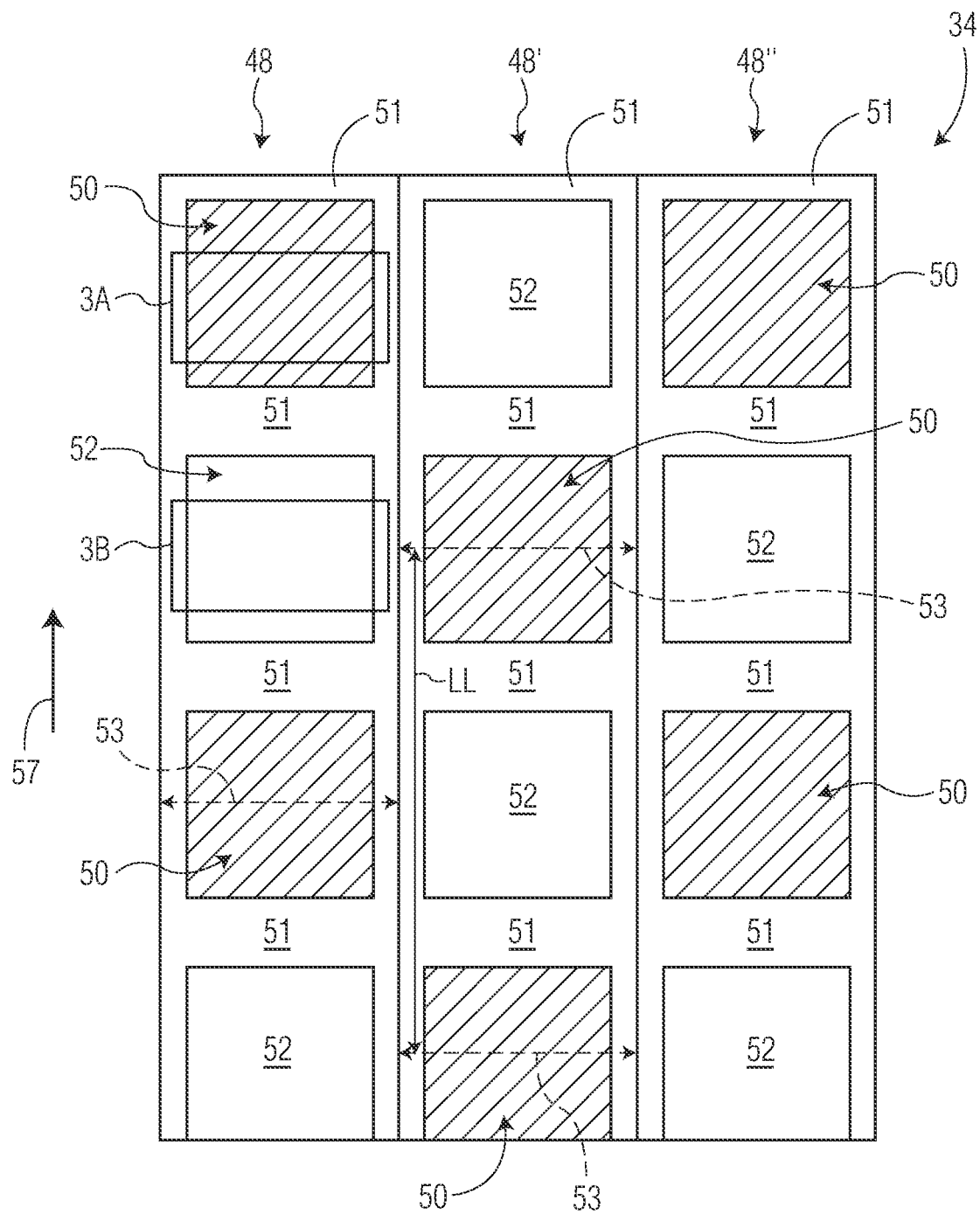
FIG. 2 is a top plan view of a surface of a pattern roll, laid flat, such as from the pattern roll used in the apparatus of FIG. 1.

In an embodiment that includes fluid entanglement, the method can include modifying the substrate 14 with a fluid entanglement apparatus 32. Whether completed off-line or in-line, the substrate 14 can be transferred to a pattern surface 34 The pattern surface 34 can be a surface of a texturizing drum 36, such as a forming screen. A portion of an exemplary pattern surface 34 will be described in greater detail below, and are shown in FIGS. 2-3B. The texturizing drum 36 can rotate as shown in FIG. 1 and can be driven by any suitable drive means (not shown) such as electric motors and gearing as are well known to those of ordinary skill in the art. The material forming the texturizing drum 36 may be any number of suitable materials commonly used for such forming drums including, but not limited to, sheet metal, plastics and other polymer materials, rubber, etc. The pattern surface 34 is perforated to allow for fluid to pass through the texturizing drum 36 and modify the substrate 14 through fluid entanglement. Typically, the pattern surface 34 is removably fitted onto and over an optional porous inner drum shell 38 so that different pattern surfaces 34 can be used for different end product designs.

The porous inner drum shell 38 interfaces with a fluid removal system 40 which facilitates pulling the entangling fluid and through the pattern surface 34, and in some patterns of the pattern surface 34, also facilitates pulling fibers of the substrate 34 through the pattern surface 34, to form three dimensional structures on the modified substrate 14', if desired. The porous inner drum shell 38 also acts as a barrier to retard further fiber movement down into the fluid removal system 40 and other portions of the equipment thereby reducing fouling of the equipment. The porous inner drum shell 38 rotates in the same direction and at the same speed as the texturizing drum 36. In addition, to further control the height of any three dimensional features on the modified substrate 14', the distance between the inner drum shell 38 and the base plane 42 (labeled in FIG. 3A) of the pattern surface 34 can be varied. Generally, the spacing between the base plane 42 of the pattern surface 34 and the outer surface of the inner drum shell 38 will range between about 0 and about 5 mm. Other ranges can be used depending on the particular end-use application and the desired features of the modified substrate 14' which will ultimately form the zoned webs 12.

The fluid entanglement apparatus 32 can include a plurality of high pressure fluid jets (not shown) to emit a plurality of pressurized fluid streams 44 from a fluid entanglement device 46. In some embodiments, there can be more than one fluid entanglement device 46. The most common fluid used in this regard is referred to as spunlace or hydroentangling technology which uses pressurized water as the fluid for entanglement. These fluid streams 44, which are preferably water, can be directed towards the substrate 14 on the pattern surface 34 and can cause the fibers to be further entangled within substrate 14 and/or the precursor forming surface 20 (in the case the precursor forming surface is an underlying web of material). As will be described in more detail below, the fluid streams 44 can modify the substrate 14 to provide a modified substrate 14'.

The entangling fluid streams 44 of the fluid entangling devices 46 emanates from injectors via jet packs or strips (not shown) consisting of a row or rows of pressurized fluid jets with small apertures of a diameter usually between 0.08 and 0.15 mm and spacing of around 0.5 mm in the cross-machine direction. The pressure in the jets can be between about 5 bar and about 400 bar but typically is less than 200 bar except for heavy nonwoven materials 10 and when fibrillation is required. Other jet sizes, spacings, numbers of jets and jet pressures can be used depending upon the particular end application. Such fluid entangling devices 66 are well known to those of ordinary skill in the art and are readily available from such manufacturers as Fleissner of Germany and Andritz-Perfojet of France.

The fluid entangling devices 46 will typically have the jet orifices positioned or spaced between about 5 mm and about 20 mm, and more typically between about 5 and about 10 mm from the pattern surface 34 though the actual spacing can vary depending on the basis weights of the materials being acted upon, the fluid pressure, the number of individual jets being used, the amount of vacuum being used via the fluid removal system 40 and the speed at which the equipment is being run.

In the embodiment shown in FIG. 1, the fluid entangling device 46 is a conventional hydroentangling device the construction and operation of which is well known to those of ordinary skill in the art, such as, for example, U.S. Pat. No. 3,485,706 to Evans, the contents of which is incorporated herein by reference in its entirety for all purposes. Also see the description of the hydraulic entanglement equipment described by Honeycomb Systems, Inc., Biddeford, Me., in the article entitled "Rotary Hydraulic Entanglement of Nonwovens", reprinted from INSIGHT '86 INTERNATIONAL ADVANCED FORMING/BONDING Conference, the contents of which is incorporated herein by reference in its entirety for all purposes.

The speed of the rotation of the drive roll 26 and the texturizing drum 36 can be set at various speeds with respect to one another. In some embodiments, the speed of the rotation of the drive roll 26 and the texturizing drum 36 can be the same. In other embodiments, the speed of the rotation of the drive roll 26 and the texturizing drum 36 can be different. For example, in some embodiments, the speed of the texturizing drum 36 may be less than the speed of the drive roll 26 to provide for overfeeding of the substrate 14 on the pattern surface 34 on the texturizing drum 36. Such overfeeding can be used to provide varied properties in the modified substrate 14'.

It should be appreciated however that other means may be used to create the pattern surface 34. For example, a foraminous belt or wire (not shown) may be used which includes holes or three-dimensional features formed in the belt or wire at appropriate locations. Alternatively, flexible rubberized belts (not shown) which are impervious to the pressurized fluid entangling streams except in the location of holes may be used. Such belts and wires are well known to those of ordinary skill in the art as are the means for driving and controlling the speed of such belts and wires.

After the fluid entanglement occurs from the fluid entangling streams 44 by the fluid entanglement device 32, the modified substrate 14' becomes a hydroentangled web with features that will be discussed in more detail below. The method 10 can further include removing the modified substrate 14' from the pattern surface 34 and drying the hydroentangled web to provide a three-dimensional nonwoven material. Drying of the material can occur through known techniques by one of ordinary skill in the art. In embodiments where the precursory web includes binder fibers, the drying of the nonwoven material can activate the binder fibers. Activating the binder fibers can assist with the preservation of the three-dimensionality of the modified substrate 14' by helping to preserve the geometry of features that extend away from the material, as will be discussed further below.

As is the case with manufacturing various materials, the modified substrate 14' can also be slit by a slitting device 15, as illustrated in FIG. 1. It can be common to manufacturing a material, such as a fluid entangled modified substrate 14' described herein, to be at a greater width than will be used in various end use applications. Thus, the modified substrate 14' can be slit by slitting techniques and apparatuses as known by those having ordinary skill in the art to provide multiple webs 12 (three such webs being shown in FIG. 1). The webs 12 can be slit in-line during the manufacturing of the modified substrate 14' or can be slit in an off-line procedure, or later as part of another manufacturing asset seeking to utilize a certain width of the modified substrate 14', and thus, one of the webs 12. The webs 12 can also be referred to as a zoned web 12, for purposes described further herein based on the features of the web 12.

Turning back the discussion to an exemplary methodology for modifying the substrate 14 in a fluid entanglement process, attention is drawn to FIG. 2. FIG. 2 illustrates a top plan view of a portion of the pattern surface 34, in which the pattern surface 34 is depicted in a laid flat orientation for purposes of clarity. The pattern surface 34 can include a plurality of pattern lanes 48, 48', 48". The pattern surface 34 includes at least two pattern lanes 48, 48'. For example, the embodiment illustrated in FIG. 2 includes three pattern lanes 48, 48', 48". The pattern lanes 48, 48', 48" can include at least two pattern zones 50, 52. For example, each pattern lane 48, 48', 48" can each include a first pattern zone 50 and a second pattern zone 52. As shown in FIG. 2, the pattern lanes 48, 48', 48" can be configured such that the first pattern zone 50 and second pattern zone 52 are adjacent to one another in the machine direction and repeating in an alternating fashion, such that each first pattern zone 50 is adjacent two second pattern zones 52 in the machine direction 22, and such that each second pattern zone 52 is adjacent two first pattern zones 50 in the machine direction 22. It is contemplated, and within the scope of the disclosure that one or more pattern lanes 48, 48', 48" can include more than two different pattern zones 50, 52.

The first pattern zone 50 can include different characteristics than the second pattern zone 52. The different characteristics between the first pattern zone 50 and the second pattern zone 52 can provide for different substrate characteristics in the modified substrate 14' that is created from the pattern surface 34 and that relate to handling characteristics of the modified substrate 14'. As an example, the first pattern zone 50 can produce a first zone 70 (labeled in FIG. 4) of the modified substrate 14' that has an open area that is greater than an open area of the second zone 72 (labeled in FIG. 4) of the modified substrate 14' produced by the second pattern zone 52. For purposes herein, "open area" refers to an amount of open area as measured by the analysis techniques in the Material Sample Analysis Test Method as described in the Test Methods section herein. Other substrate characteristics that could differ between the first zone 70 and the second zone 72 of the modified substrate 14' that are produced by the first pattern zone 50 and the second pattern zone 52, respectively, can provide different web handling characteristics of the modified substrate 14' and can include, for example, differences in basis weight, density, tensile strength, bulk thickness, surface texture, and/or urine wicking properties, among other characteristics.

Figure 3A:
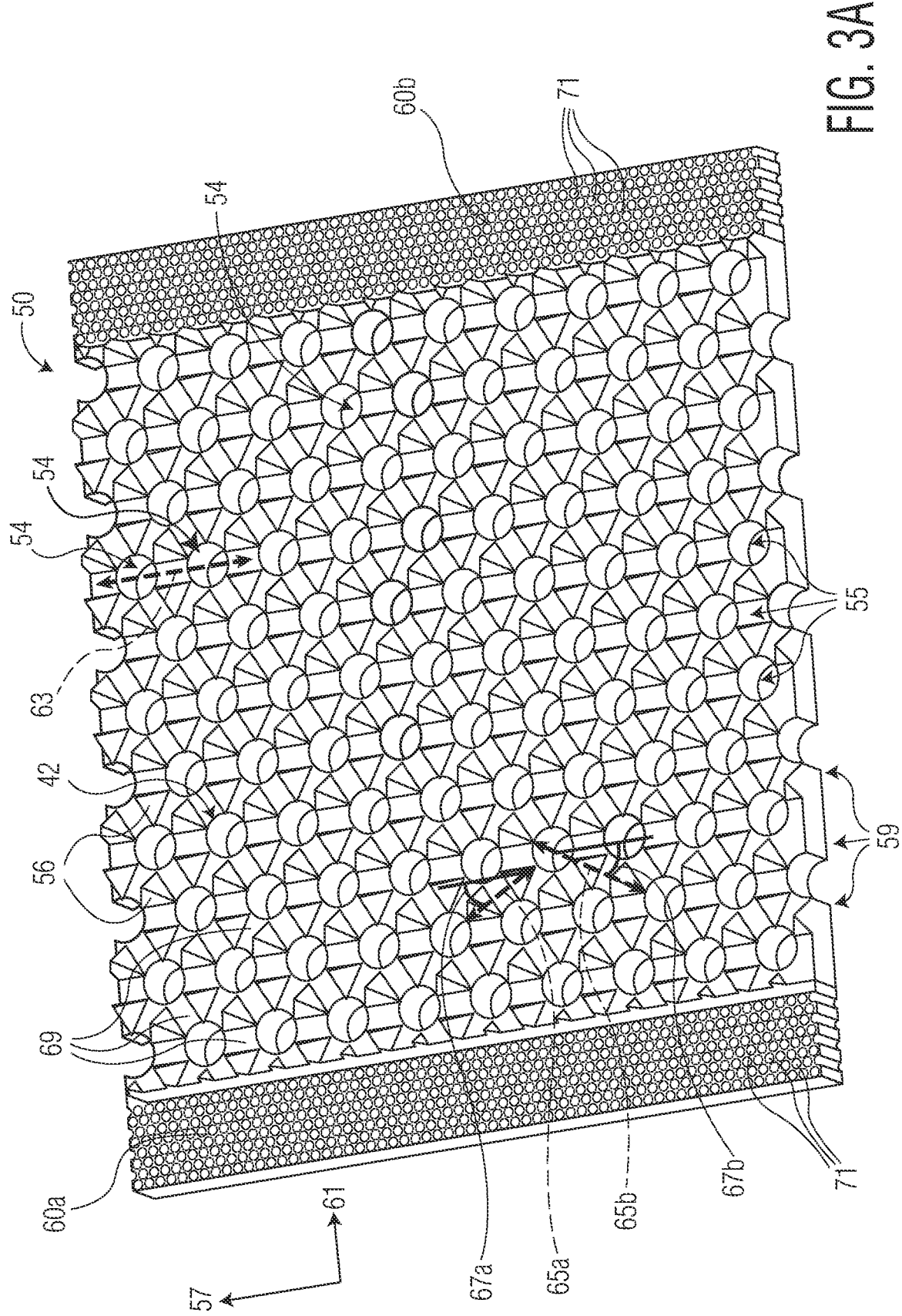
FIG. 3A is a detailed view of a first pattern zone of the pattern roll taken from FIG. 2.
Figure 3B:
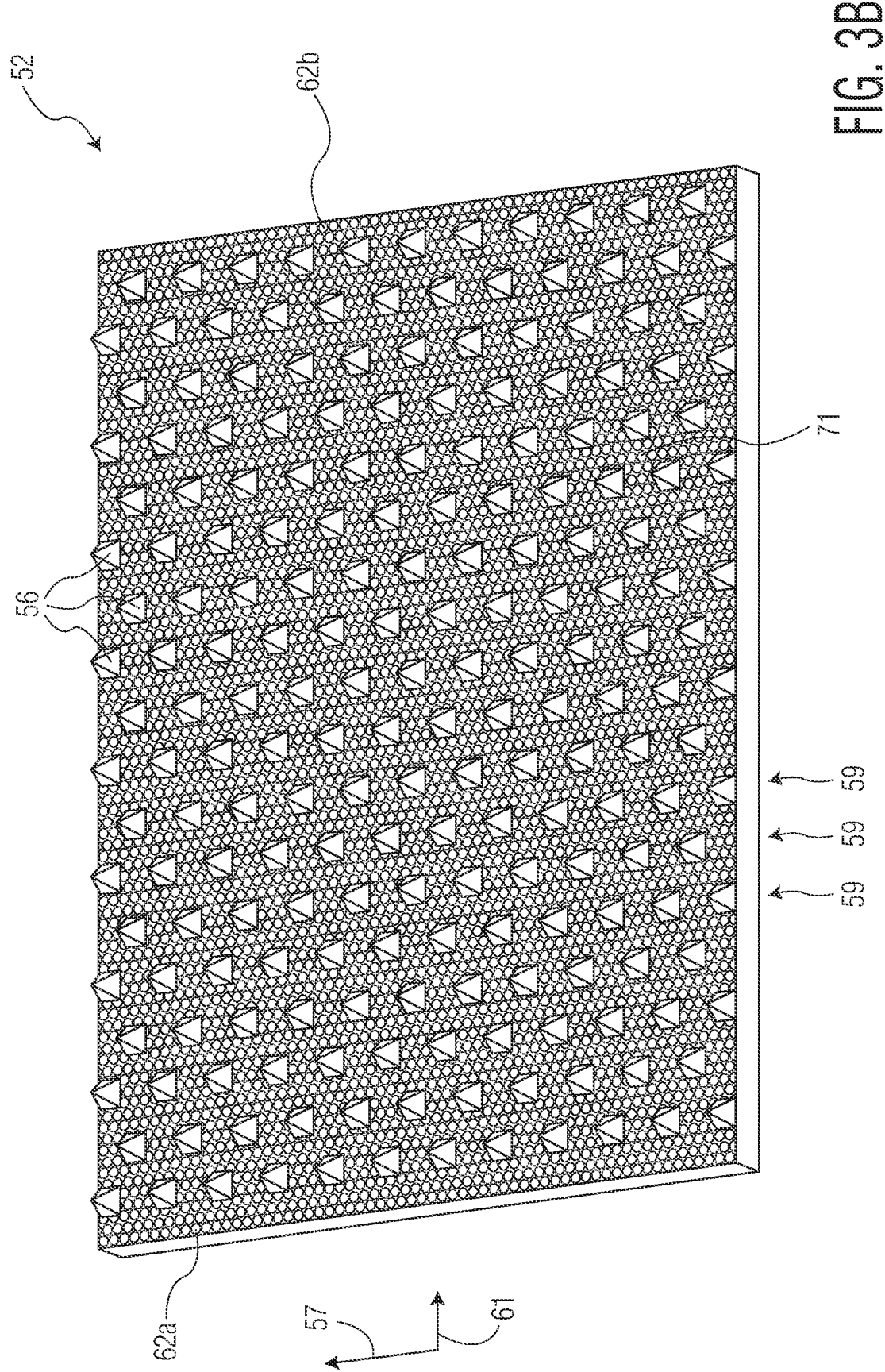
FIG. 3B is a detailed view of a second pattern zone of the pattern roll taken from FIG. 2.

FIG. 3A provides a detailed portion of the first pattern zone 50 of the pattern surface 34 from the first pattern lane 48 from the exemplary pattern surface 34 of FIG. 2. In a preferred embodiment, the first pattern zone 50 of the pattern surface 34 can include a plurality of forming holes 54, a plurality of projections 56, and a plurality of connecting ligament forming areas 69. The connecting ligament forming areas 69 can be disposed between the plurality of forming holes 54 and the plurality of projections 56 and can generally be areas of the pattern surface 34 that are neither a forming hole 54 nor a projection 56.

As will be discussed in more detail below, the geometry, spacing, and orientation of the forming holes 54, the projections 56, and the connecting ligament forming areas 69 will correspond to the formation of the nodes 74, openings 76, and connecting ligaments 78 in the modified substrate 14'. The alignment and orientation of these forming holes 54, projections 56, and connecting ligament areas 69 can provide for beneficial properties in the formation of the modified substrate 14' as described herein. For example, particular alignments and orientations can help to produce desired tensile strength properties and/or desired necking properties for processability of the materials, while still allowing for a highly-open material and thus achieving beneficial fluid-handling properties. Although such alignments and orientations are described with respect to the specific pattern of the first zone pattern 50 of the pattern surface 34 in FIG. 3A, it should be understood that other patterns for the first pattern zone 50 for pattern surfaces are contemplated by the present disclosure and may achieve such described alignments and orientations in other patterns.

As depicted in FIG. 3A, the first pattern zone 50 of the pattern surface 34 can include a plurality of forming holes 54 that correspond to the shape and pattern of the nodes 74 of the modified substrate 14'. While the forming holes 54 depicted in FIG. 3A are round, it should be understood that any number of shapes and combination of shapes can be used depending on the end use application. Examples of additional or alternative possible forming hole 54 shapes include, but are not limited to, ovals, crosses, squares, rectangles, diamond shapes, hexagons and other polygons.

The forming holes 54 can be arranged in a plurality of lanes 55 (three lanes 55 labeled in FIG. 3A) that extend in the longitudinal direction 57 of the pattern surface 34. The longitudinal direction 57 of the pattern surface 34 can correspond to a circumferential direction, for example, if the pattern surface 34 is part of a cylindrical texturizing drum 36. The lanes 55 of forming holes 54 can be formed of longitudinally adjacent forming holes 54. Forming holes 54 are longitudinally adjacent if a line 63 drawn between centers of forming holes 54 does not pass through any projections 56 or any other forming holes 54 and forms an angle with respect to the longitudinal direction 57 of less than forty-five degrees. Similarly, the forming holes 54 can also be arranged in lanes that extend in the lateral direction 61 of the pattern surface 34 if a line drawn between centers of forming holes 54 does not pass through any projections 56 or any other forming holes 54 and forms an angle with respect to the lateral direction 61 of the pattern surface 34 of less than forty-five degrees. The orientation of the forming holes 54 in the pattern surface 34 determines the orientation of the nodes 74 in the modified substrate 14', as fibers from the substrate 14 are pushed into the forming holes 54 by the fluid jets 44 during fluid entanglement discussed above.

Where lines drawn between centers of two or more forming holes 54 and a center of a connected, longitudinally adjacent forming hole 54, each form an angle with respect to the longitudinal direction 57 of the pattern surface 34 of less than about twenty degrees, the connected, longitudinally adjacent forming hole 54 which is considered to be in the lane 55 with the reference forming hole 54 is the connected, longitudinally adjacent forming hole 54 for which the line drawn between its center and the center of the reference forming hole 54 forms the smaller angle. Where the lines drawn between the centers of the connected, longitudinally adjacent forming holes 54 and a center of the reference forming hole 54 form angles with respect to the longitudinal direction 57 of the pattern surface 34 which are equal, the lane 55 ends and none of the connected, longitudinally adjacent forming holes 54 are considered to be part of that particular lane 55 with the reference forming hole 54.

A lane 55 of forming holes 54 includes a series of connected, longitudinally adjacent forming holes 54. It may be preferable for one or more lanes 55 of forming holes 54 to be configured to extend substantially in the longitudinal direction 57. A lane 55 is considered to extend in the longitudinal direction when lines (such as line 63) drawn between centers of longitudinally adjacent forming holes 54 forms an angle with respect to the longitudinal direction 57 of less than about twenty degrees, more preferably less than about fifteen degrees, even more preferably less than about ten degrees, and still even more preferably less than about five degrees. No angle is shown in FIG. 3A because the angle formed by line 63 with respect to the longitudinal direction 57 is zero degrees. In some preferred embodiments, a majority of the plurality of lanes 55 of forming holes 54 that are arranged in the longitudinal direction 57 can be configured to extend substantially in the longitudinal direction 57. Some embodiments, such as that depicted in FIG. 3A, may have all the lanes 55 of forming holes 54 on the pattern surface 34 configured in such a fashion.

In some embodiments, it may be preferable for the first pattern zone 50 of the pattern surface 34 to have at least three lanes 55 of forming holes 54 which extend substantially in the longitudinal direction 57 of the pattern surface 34, or at least four lanes 55 which extend substantially in the longitudinal direction 57, or at least five lanes 55 which extend substantially in the longitudinal direction 57, or at least six lanes 55 which extend substantially in the longitudinal direction 57, or at least seven or eight lanes 55 which extend substantially in the longitudinal direction 57.

The lanes 55 of forming holes 54 that extend substantially in the longitudinal direction 57 of the pattern surface 34 can have a length that spans the entire machine directional length of the first pattern zone 50 of the pattern surface 34 or can form only a portion of the pattern surface 34 length in the longitudinal direction 57 (such as a portion of the circumference of the pattern surface 34).

The pattern surface 34 can also include a plurality of projections 56 extending away from the base plane 42 of the pattern surface 34. As depicted in FIG. 3A, the projections 56 can be configured in a pyramidal geometry, however, the projections 56 can be in various other geometries, cross-sectional shapes, spacings, and orientations. In some embodiments, the plurality of projections 56 can decrease in cross-sectional area as they extend further away from the base plane 42 of the pattern surface 34. For example, the pyramidal shape of the projections 56 depicted in FIG. 3A decrease in area the further the projection 56 extends away from the base plane 42 of the pattern surface 34.

Overall, the alignment of the forming holes 54 to form lanes 55 of forming holes 54 extending substantially in the longitudinal direction 57 can align connecting ligament forming areas 69 in the longitudinal direction 57. For example, the lines 63 drawn between centers of longitudinally adjacent forming holes 54 may approximate the location and directions of connecting ligament forming areas 69 which connect such longitudinally adjacent forming holes 54. By having such lanes 55 of forming holes 54 which extend substantially in the longitudinal direction 57, at least some of the connecting ligament forming areas 69 may be substantially longitudinally aligned. These substantially longitudinally aligned connecting ligament forming areas 69 can lead to a first pattern zone 50 of the modified substrate 14' that can provide beneficial tensile strength and/or reduced necking properties yet maintain an adequate percent open area.

The projections 56 can be arranged in a plurality of lanes 59 (three lanes 59 labeled in FIG. 3A) that extend in the longitudinal direction 57 of the pattern surface 34. The lanes 59 of projections 56 can be formed of a series of connected, longitudinally adjacent projections 56. Projections 56 are longitudinally adjacent where a line (such as line 65a or 65b in FIG. 3A) does not pass through any forming holes 54 or any other projections 56 and spans across only a single connecting ligament forming area 69 and forms an angle with respect to the longitudinal direction 57 of the pattern surface 34 of less than about forty-five degrees. The centers of the projections 56 may be the geometric centers of the projections 56. Similarly, the projections 56 can also be laterally adjacent when if a line drawn between centers of projections 56 does not pass through any forming holes 54 or any other projections 56 and the line only spans across a single connecting ligament forming area 69 and forms an angle with respect to the lateral direction 61 of the pattern surface 34 of less than forty-five degrees.

In some embodiments, a majority of the plurality of lanes 59 of projections 56 extending in the longitudinal direction 57 are laterally offset from a nearest adjacent lane 55 of forming holes 54 extending substantially in the longitudinal direction 57. With such a configuration, such as depicted in FIG. 3A, the connecting ligament forming areas 69 disposed between forming holes 54 can extend substantially in the longitudinal direction 57. As a result, first zones 72 of modified substrates 14' formed from such a first pattern zone 50 of the pattern surface 34 can have connecting ligaments 78 that extend substantially in the longitudinal direction of the modified substrate 14'. As noted above, this can provide beneficial properties of improved tensile strength and reduced necking of the first zone 70 of the modified substrate 14' while maintaining a desirable percent open area of the first zone 70 of the modified substrate 14'.

In some embodiments, the projections 56 within each lane 59 can be configured such that longitudinally adjacent projections 56 can form a line 65a or 65b that forms an angle 67a, 67b, respectively, with the longitudinal direction 57. In some embodiments, this angle 67a or 67b can be between 15 degrees to 60 degrees. As depicted in FIG. 3A, longitudinally adjacent projections 56 within a lane 59 of projections 56 can form a zig-zag type pattern in the longitudinal direction 57 such that each projection 56 within a single lane 59 of projections 56 is laterally offset in the lateral direction 61 from its prior projection 56 and its successive projection 56 in the lane 59 in the same lateral direction 61.

The orientation of the projections 56 in the first pattern zone 50 of the pattern surface 34 determines the orientation of the openings 76 in the first zone 70 of the modified substrate 14' (labeled in FIG. 4), as fibers from the substrate 14 are pushed around the projections 56 in the first pattern zone 50 by the fluid jets 44 during fluid entanglement discussed above.

In some embodiments, on the lateral sides of the first pattern zone 50, the pattern surface 34 can include one or more areas 60a, 60b that are substantially free from projections 56. The areas 60a, 60b can correspond to the side zones 80a, 80b in the modified substrate 14' (two side zones 80a, 80b labeled in FIG. 4). In some embodiments, the areas 60a, 60b corresponding to the side zones 80a, 80b can include apertures 71. However, in preferred embodiments, if included, the apertures 71 in the areas 60a, 60b are smaller in cross-sectional area than the forming holes 54 in the first pattern zone 50 of the pattern surface 34 and can help with fluid removal during the fluid entangling process. For example, an average area of the apertures 71 in the areas 60a, 60b can be less than an average area of the forming holes 54 in the first pattern zone 50. In some embodiments, an average area of the apertures 71 can be between about 1.0 mm to about 1.5 mm. Depending on the density of the apertures 71 in the areas 60a, 60b and the area of the apertures 70, in some embodiments, the apertures 71 can provide from about 15% to about 50% of the area of the areas 60a, 60b. The apertures 71 in the areas 60a, 60b can lead to formation of micro-bumps in the modified substrate 14'. The area of the base plane 42 of the forming surface 50 between the apertures 71 in zones 60a, 60b can form micro-apertures and/or areas of lower fiber density in the modified substrate 14'.

Turning now to FIG. 3B, a portion of the second pattern zone 52 of the pattern surface 34 of FIG. 2 is illustrated. The second pattern zone 52 can include projections 56 that extend away from the base plane 42 of the pattern surface 34. The projections 56 in the second pattern zone 52 can be the same size and/or height as the projections 56 in the first pattern zone 50. In some embodiments, the projections 56 in the second pattern zone 52 can be a different size and/or height as the projections 56 in the first pattern zone 50.

The projections 56 can be arranged in a plurality of lanes 59 (three lanes 59 labeled in FIG. 3B) that extend in the longitudinal direction 57 of the pattern surface 34. The lanes 59 of projections 56 can be formed of a series of connected, longitudinally adjacent projections 56, as described above with respect to the projections 56 in the first pattern zone 50 of the pattern surface 34. In some embodiments, the first pattern zones 50 can include six, seven, or eight or more lanes 59 of projections 56 extending in the longitudinal direction 57. In some embodiments, a majority of the plurality of lanes 59 of projections 56 extending in the longitudinal direction 57 are laterally offset from a nearest adjacent lane 55 of forming holes 54 extending substantially in the longitudinal direction 57.

The projections 56 in the second pattern zone 52 of the pattern surface 34 can form the openings 76 in the second zone 72 of the modified substrate 14' (labeled in FIG. 4), as fibers from the substrate 14 are pushed around the projections 56 in the second pattern zone 52 by the fluid jets 44 during fluid entanglement discussed above. Thus, the orientation, density, and size of the projections 56 in the second pattern zone 52 of the pattern surface 34 correspond to the orientation, density, and size of the openings 76 in the second zone 72 of the modified substrate 14'.

In a preferred embodiment, the total number and/or size of projections 56 in the second pattern zone 52 of the pattern surface 34 and the total number and/or size of projections 56 in the first pattern zone 50 of pattern surface 34 are configured with respect to one another such that an open area of the first zone 70 of the modified substrate 14' is greater than an open area of the second zone 72 of the modified substrate 14'. In a preferred embodiment, the total number of projections 56 in the second pattern zone 52 is greater than the total number of projections in the first pattern zone 50, but the projections 56 in the second pattern zone 52 are smaller in area than the projections 56 in the first pattern zone 50, such that the open area of the first zone 70 of the modified substrate 14' is greater than an open area of the second zone 72 of the modified substrate 14'.

In some embodiments, on the lateral sides the second pattern zone 52, the pattern surface 34 can include one or more areas 62a, 62b that are substantially free from projections 56. The areas 62a, 62b can correspond to the side zones 82a, 82b in the modified substrate 14' (two side zones 82a, 82b labeled in FIG. 4). In some embodiments, the areas 62a, 62b corresponding to the side zones 80a, 80b can include apertures 71. However, in preferred embodiments, if included, the apertures 71 in the areas 62a, 62b are smaller in cross-sectional area than the forming holes 54 in the first pattern zone 50 of the pattern surface 34 and can help with fluid removal during the fluid entangling process. For example, an average area of the apertures 71 in the areas 62a, 62b can be less than an average area of the forming holes 54 in the first pattern zone 50. The apertures 71 in the areas 62a, 62b can lead to formation of micro-bumps in the modified substrate 14'.

The second pattern zone 52 of the pattern surface 34 can also include a plurality of apertures 71 disposed between projections 56 in the second pattern zone 52. The apertures 71 in the second pattern zone 52 can be similar to the apertures 71 described above with respect to areas 62a, 62b on the lateral sides of the second pattern zone 52. The apertures 71 can help with fluid management during the fluid entanglement process. In some embodiments, the second pattern zone 52 can be configured to not include any apertures 71.

As illustrated in FIG. 2, in some embodiments, the pattern surface 34 can also include one or more transition pattern zones 51. A transition pattern zone 51 in the pattern surface 34 can be disposed between the first pattern zone 50 and the second pattern zone 52 in the longitudinal direction 57 of the pattern surface 34. The transition pattern zone 51 can be an area of the pattern surface 34 that is free from projections 56 or at least has less projections 56 than the first pattern zone 50. In some embodiments, the transition pattern zone 51 can include apertures similar to the apertures 71 described above with respect to areas 60a, 60b on the lateral sides of the first pattern zone 50. The transition pattern zone 51 of the pattern surface 34 can correspond to the transition zone 73 (labeled in FIG. 4) of the modified substrate 14' after the substrate 14 is modified by the fluid entanglement apparatus 32. Although not depicted, in some embodiments, the transition pattern zone 51 can also include forming holes 54 such as described above with respect to the first pattern zone 50.

In a preferred embodiment, the pattern lanes 48, 48', 48" can be configured such that the first pattern zone 50 in the first pattern lane 48 is substantially the same as the first pattern zone 50 in the second pattern lane 48'. In some embodiments, the first pattern zone 50 in the third pattern lane 48" can be substantially the same as the first pattern zone 50 in the second pattern lane 48' and/or substantially the same as the first pattern zone 50 in the first pattern lane 48. Similarly, in some embodiments, the pattern lanes 48, 48', 48" can be configured such that the second pattern zone 52 in the first pattern lane 48 is substantially the same as the second pattern zone 52 in the second pattern lane 48'. In some embodiments, the second pattern zone 52 in the third pattern lane 48" can be substantially the same as the second pattern zone 52 in the second pattern lane 48' and/or substantially the same as the second pattern zone 52 in the first pattern lane 48.

Alternatively, it is contemplated that the first pattern zone 50 in the first pattern lane 48 can be configured differently than the first pattern zone 50 in a second pattern lane 48' and/or the first pattern zone 50 in the third pattern lane 48". It is also contemplated that the second pattern zone 52 in the first pattern lane 48 can be configured to be different from the second pattern zone 52 in the second pattern lane 48' and/or the second pattern zone 52 in the third pattern lane 48".

Figure 4:
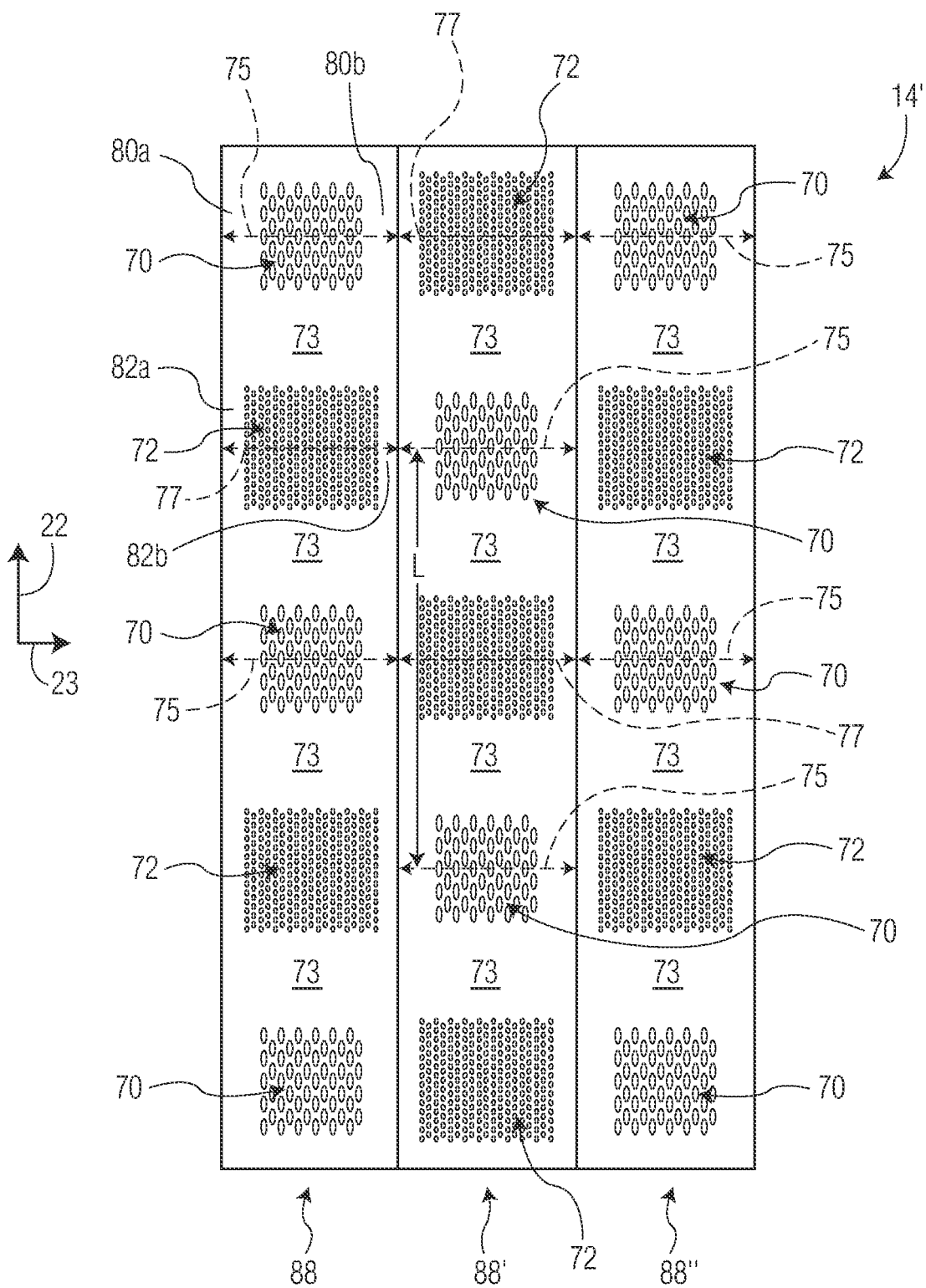
FIG. 4 is a top plan view of a portion of an exemplary modified substrate that can be formed from the apparatus of FIG. 1, the modified substrate including three lanes including a plurality of first zones and a plurality of second zones, with the lanes being produced such that the first zones are staggered in a machine direction between adjacent lanes.

Turning to FIG. 4, based on the configuration of the pattern surface 34 described above, the substrate 14 is modified by the fluid entanglement device 46 to provide a modified substrate 14'. The modified substrate 14' can include a first lane 88, a second lane 88', and a third lane 88" that are parallel to one another. The first lane 88 can be provided by the fluid entanglement of the substrate 14 over the first pattern lane 48 of the pattern surface 34. The second lane 88' can be provided by the fluid entanglement of the substrate 14 over the second pattern lane 48' of the pattern surface 34. The third lane 88" can be provided by the fluid entanglement of the substrate 14 over the third pattern lane 48" of the pattern surface 34.

The first lane 88 of the modified substrate 14' can include a plurality of first zones 70 that are provided by the fluid entanglement over the respective first pattern zones 50 in the first pattern lane 48 of the pattern surface 34. The first lane 88 of the modified substrate 14' can also include a plurality of second zones 72 that are provided by the fluid entanglement over the respective second pattern zones 52 in the first pattern lane 48 of the pattern surface 34. The second lane 88' of the modified substrate 14' can include a plurality of first zones 70 that are provided by the fluid entanglement over the respective first pattern zones 50 in the second pattern lane 48' of the pattern surface 34. The second lane 88' of the modified substrate 14' can also include a plurality of second zones 72 that are provided by the fluid entanglement over the respective second pattern zones 52 in the second pattern lane 48' of the pattern surface 34. Similarly, the third lane 88" of the modified substrate 14' can include a plurality of first zones 70 that are provided by the fluid entanglement over the respective first pattern zones 50 in the third pattern lane 48" of the pattern surface 34. The third lane 88" of the modified substrate 14' can also include a plurality of second zones 72 that are provided by the fluid entanglement over the respective second pattern zones 52 in the third pattern lane 48" of the pattern surface 34.

The modified substrate 14' can also include transition zones 73 in one or more lanes 88, 88', 88". As illustrated in FIG. 4, the transition zones 73 in the modified substrate 14' can be disposed between adjacent first and second zones 70, 72 in each lane 88, 88', 88". As discussed above, the transition zones 73 in the lanes 88, 88', 88" of the modified substrate 14' can be provided by the transition pattern zones 51 in the corresponding pattern lanes 48, 48', 48" of the pattern surface 34. The transition zones 73 preferably include less open area than the first zone 70 and the second zone 72 of the modified substrate 14'.

Figure 5A:
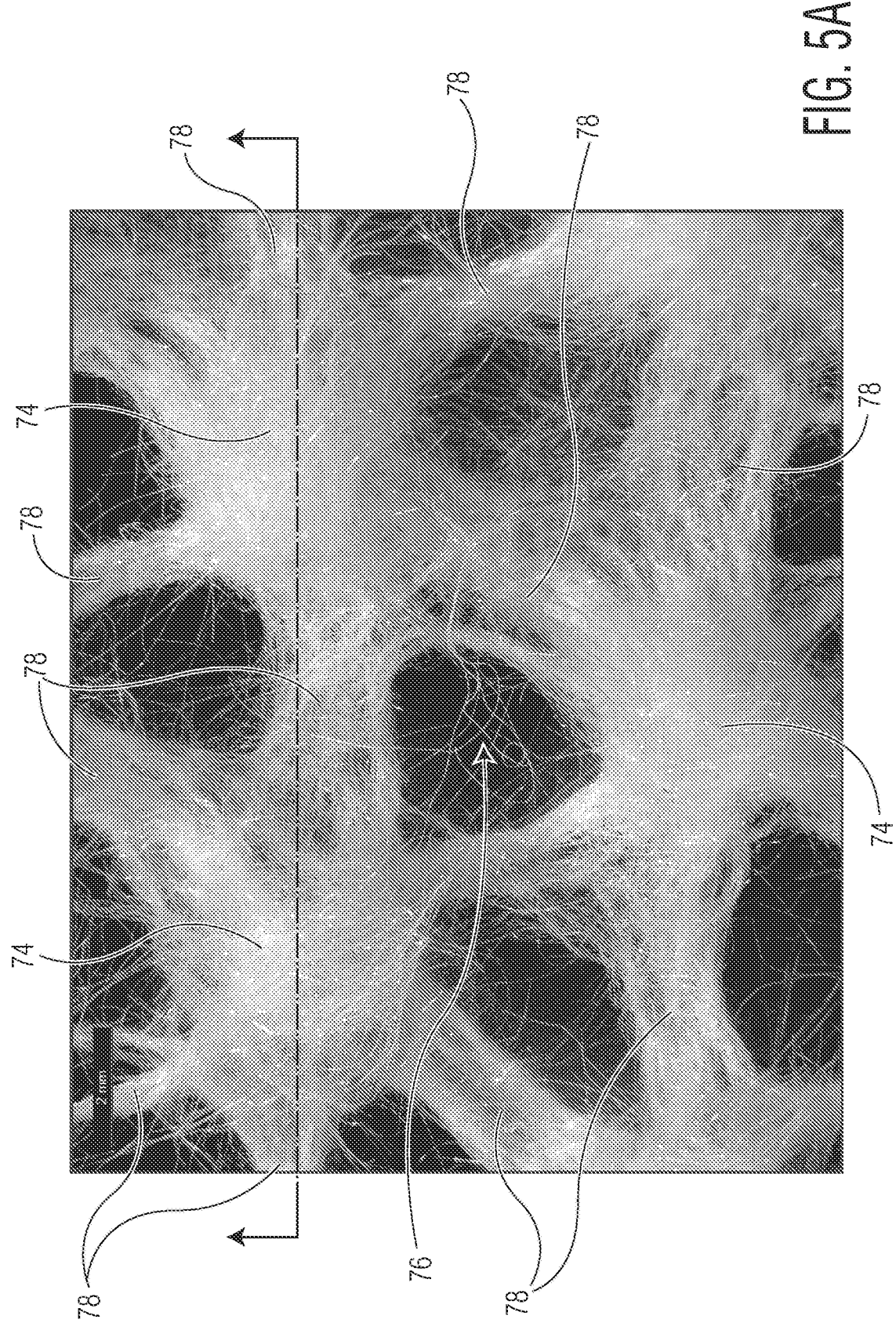
FIG. 5A is a Scanning Electron Microscope (SEM) image providing a detailed view of a first zone taken from the exemplary modified substrate of FIG. 4.

FIG. 5A illustrates a Scanning Electron Microscope (SEM) image of a portion of the first zone 70 of the modified substrate 14'. As discussed above, the first zone 70 of the modified substrate 14' can include openings 76. As discussed above, the openings 76 in the first zone 70 of the modified substrate 14' are produced by fibers being pushed around the projections 56 in the first pattern zone 50 of the pattern surface 34 during fluid entanglement. The openings 76 can be formed between the plurality of connecting ligaments 78 and the plurality of nodes 74. Individual openings 76 can be disposed between adjacent nodes 74. Individual openings 76 can be defined between at least three connecting ligaments 78 and at least three nodes 74. In some embodiments, a majority of the plurality of openings 76 can be configured such that each has an area (as measured by the area of the opening 24 within the base plane of the modified substrate 14') that ranges from about 5 mm$^2$ to about 25 mm$^2$, more preferably from about 7 mm$^2$ to about 20 mm$^2$, and even more preferably, from about 7 mm$^2$ to about 17 mm$^2$. The area of the openings 76 within the first zone 70 can be measured using the analysis techniques in the Material Sample Analysis Test Method as described in the Test Methods section herein.

The openings 76 in the first zone 70 of the modified substrate 14' can help provide beneficial open area for various fluid applications. In some embodiments, the plurality of openings 76 for the modified substrate 14' can help provide a percent open area for the first zone 70 from about 10% to about 60%. In some preferred embodiments, the plurality of openings 76 for the first zone 70 can help provide a percent open area for the first zone 70 from about 15% to about 45%, or from about 20% to about 40%, or from about 20% to about 30%. As mentioned above, the percent open area (also referred to as open area) is determined using the Material Sample Analysis Test Method as described in the Test Methods section herein. Although it is described in detail in the Test Methods section, the Material Sample Analysis Test Method involves projecting a light source on the material such that the openings 76 can be identified by the property that the openings 76 allow a greater percentage of light to pass through the material, which is illustrated in the SEM image of FIG. 5A.

The plurality of openings 76 can provide a variety of beneficial properties to the modified substrate 14'. For example, the openings 76 can provide enhanced fluid transfer for the modified substrate 14' and/or increased permeability. As an example, if the modified substrate 14', after processing into a zoned web 12, is utilized in an article that intakes and distributes fluid, the openings 76 can help provide increased intake and distribution of fluids through and/or across the modified substrate 14'. In particular, the plurality of openings 76 can enhance the ability of a material to intake and distribute BM material (also referred to herein as feces or fecal matter), resulting in less pooling of the BM on the material and therefore less BM disposed against a skin of a wearer of an absorbent article comprising such nonwoven material.

The first zone 70 can also include nodes 74 that provide three dimensionality to the modified substrate 14'. The nodes 74 are provided by fibers in the substrate 14 being pushed into the forming holes 54 of the first pattern zone 54 of the forming surface 34 in the fluid entanglement process. The shape of the nodes 74 in the modified substrate 14' can be varied by adjusting the shape of the forming holes 54 in the first pattern zone 50 of the pattern surface 34. The depth of the forming holes 54 in the first pattern zone 50 of the pattern surface 34 can influence the height of the nodes 74 that are created in the first zone 70 of the modified substrate 14'. In some embodiments, the nodes 74 can have a height between 1 mm and 10 mm but preferably between around 3 mm and 6 mm to produce nodes 74 with the shape most useful in the expected common applications for personal care absorbent articles. The diameter of the nodes 74 can be controlled by the diameter of the forming hole 54 cross-section diameter (or major dimension), which may be between about 2 mm and 10 mm but it is preferably between 3 mm and 6 mm. The nodes 74 can have a cross-sectional area of about 5 mm$^2$ to about 35 mm$^2$ at their widest cross-sectional area, and more preferably, from about 10 mm$^2$ to about 20 mm$^2$. The plurality of nodes 74 can be configured in the first zone 70 of the modified substrate 14' to provide a node density of about 1.0 nodes/cm$^2$ to about 3.0 nodes/cm$^2$. In preferred embodiment in which the first zone 70 of the modified substrate 14' forms a portion of an absorbent article, such as a bodyside liner, the nodes 74 can provide important fluid control, preventing insults (such as urine and BM) from spreading on the liner, as well as comfort against the user's skin.

The first zone 70 of the modified substrate 14' can also include connecting ligaments 78, as best illustrated in the detailed SEM view shown in FIG. 5A. The connecting ligaments 78 can connect adjacent nodes 74 in the modified substrate 14'. The connecting ligaments 78 in the modified substrate 14' can be formed by the fluid streams 44 directing the fibers of the substrate 14 around the projections 56 in the first pattern zone 50 of the pattern surface 34 and into the connecting ligament forming areas 69 of the first pattern zone 50 of the pattern surface 34. An individual connecting ligament 78 can be referred to as extending between only two adjacent nodes 74. In other words, an individual connecting ligament 78 does not interconnect three or more nodes 74. In preferred embodiments, a majority of the plurality of nodes 74 in the first zone 70 can include at least three connecting ligaments 78 connecting to adjacent nodes 74. In preferred embodiments, a majority of the plurality of nodes 74 in the first zone 70 can include ten or less connecting ligaments 78 connecting to adjacent nodes 74. In some embodiments, modified substrate 14' can be configured such that a majority of the plurality of nodes 74 in the first zone 70 can include three to eight connecting ligaments 78 connecting to adjacent nodes 74.

Figure 5B:
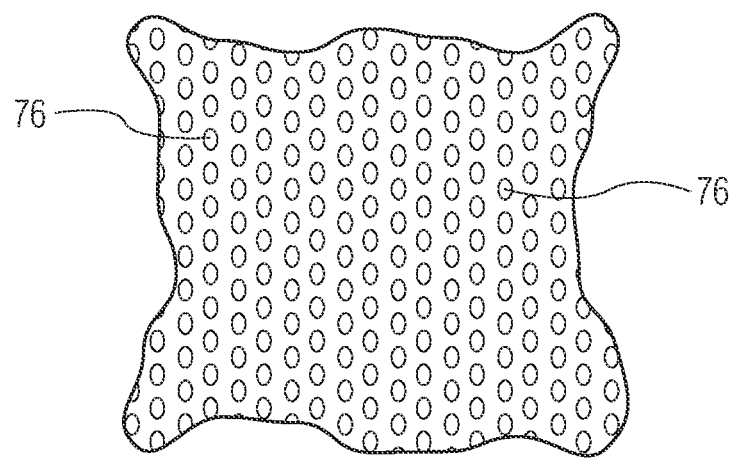
FIG. 5B is a detailed view of a second zone taken from the exemplary modified substrate of FIG. 4.

In a preferred embodiment, the second zone 72 of the modified substrate 14' can also include openings 76, as best shown in FIG. 5B. The openings 76 in the second zone 72 of the modified substrate 14' are created similar to the openings 76 in the first zone 70, in that fibers of the substrate 14 are pushed around the projections 56 in the second pattern zone 52 of the pattern surface 34 during fluid entanglement. The openings 76 can provide for an open area of from about 1% to about 30% in some embodiments, or from about 2% to about 20%, or from about 3% to about 15%. Preferably, the open area of the second zone 72 is less than the open area of the first zone 70 of the modified substrate 14'.

Where the modified substrate 14' is a fluid entangled material, it has been found that the percent open area values of the side zones 80a, 80b, 82a, 82b and the transition zones 73 may generally be greater than about 0.5%, or greater than about 0.6%, or greater than about 0.7% or greater than about 0.8%, or greater than about 0.9%, or greater than about 1.0%, or greater than about 1.25%, or greater than about 2.5%, as determined according to the Material Sample Analysis Test Method. It has been found that the percent open area values of the side zones 80a, 80b, 82a, 82b and the transition zones 73 in the fluid-entangled nonwoven materials of the present disclosure, such as modified substrate 14', are generally greater than the percent open area values of conventional nonwoven materials of similar basis weights, such as spunbond materials, meltblown materials, and even spunlace materials, which do not have openings and/or projections or whereby the openings and/or projections are not formed integrally during formation of such materials.

Importantly, the modified substrate 14' is configured such that the first zone 70 of the first lane 88 is staggered in the machine direction 22 from the first zone 70 of the second lane 88'. As used herein, "staggered in the machine direction" means that a cross-directional centerline 75 of the first zone 70 in a specified lane 88, 88', 88" is off-set in the machine direction 22 from a cross-directional centerline 75 of the nearest first zones 70 in the adjacent lane 88, 88', 88". The staggering of first zones 70 between adjacent lanes (for example, lanes 88, 88') provides for more balanced web handling of the modified substrate 14', particularly when the modified substrate 14' includes a plurality of lanes 88, 88', 88" each with a plurality of different zones 70, 72 that have different handling characteristics. For example, in the fluid-entangled modified substrate 14' described herein, the first zone 70 could have an open area (also referred to as percent open area) that is greater than the open area of the second zone 72. As noted above, an exemplary open area for the first zone 70 could be 30% and the open area for the second zone 72 could be 10%. By having different open areas, the first zone 70 and the second zone 72 have different substrate handling characteristics. Other embodiments contemplated by the present disclosure could have a first zone 70 and second zone 72 having different substrate handling characteristics for reasons alternative to or in addition to different open areas. When a plurality of lanes 88, 88', 88" including different zones 70, 72 that have different substrate handling characteristics are formed together in the modified substrate 14', difficulties can exist in web handling. Machine directional staggering of the first zones 70 between adjacent lanes 88, 88'has been found to significantly improve web handling of the modified substrate 14', such as by reducing web curl and web breaks.

As depicted in FIG. 4, the first lane 88 and the second lane 88' can be configured such that a majority of the first zones 70 in the first lane 88 are staggered in the machine direction 22 from a majority of the nearest first zones 70 in the second lane 88'. Preferably, substantially all, or all of the first zones 70 in the first lane 88 are staggered in the machine direction 22 from substantially all, or all of the nearest adjacent first zones 70 in the second lane 88'. As illustrated in FIG. 4, a first zone 70 in the first lane 88 can be staggered in the machine direction 22 from nearest adjacent first zones 70 in the second lane 88 such that the cross-directional centerline 75 of the first zone 70 in the first lane 88 is disposed at a machine direction off-set to the centerlines 75 of the nearest adjacent first zones 70 in the second lane 88' by being between 20%-80% of a machine direction length L between successive first zones 70 in the second lane 88'.

To help explain this machine directional off-set preferred range, a few examples will be discussed. If a first zone 70 in the first lane 88 was not staggered in the machine direction 22 from a nearest adjacent first zone 70 in the second lane 88', the cross-directional centerline 75 of the first zone 70 in the first lane 88 would be co-linear with the cross-directional centerline 75 of the nearest adjacent first zone 70 in the second lane 88', which could alternatively be described as the first zone 70 in the first lane 88 having its centerline 75 being disposed at 0% off-set of the machine direction length L as compared to the centerline 75 of the nearest adjacent first zone 70 in the second lane 88'.

In another example, such as for the embodiment depicted in FIG. 4, the first zones 70 in the first lane 88 are disposed such that they are evenly staggered in the machine direction 22 from adjacent first zones 70 in the second lane 88', which provides that the cross-directional centerline 75 of each first zone 70 in the first lane 88 is disposed at a machine direction off-set of 50% of a machine direction length L of the repeating first zones 70 in the second lane 88'. Thus, the repeating patterns of the first zones 70 and second zones 72 of the two lanes 88, 88' could be adjusted to have a different percentage of staggering in the machine direction 22 within this range by adjusting the phasing of the first zones 70 between the first lane 88 with respect to the second lane 88', or vice versa.

As depicted in FIG. 4, the first zones 70 in the second lane 88' can be staggered from the first zones 70 in the third lane 88". In some embodiments, such as the embodiment depicted in FIG. 4, the cross-directional centerlines 75 of the first zones 70 in the first lane 88 can align with respective cross-directional centerlines 75 of the first zones 70 in the third lane 88" in the machine direction 22. Thus, the machine directional staggering of the first zones 70 in the first lane 88 from the first zones 70 in the second lane 88' can be the same as the machine directional staggering of the first zones 70 in the second lane 88' from the first zones 70 in the third lane 88".

By having the first zones 70 in the first lane 88 staggered in the machine direction 22 from the nearest adjacent first zones 70 in the second lane 88', the second zones 72 in the first lane 88 can also be similarly staggered in the machine direction 22 from the nearest adjacent second zones 72 in the second lane 88'. For example, the cross-directional centerline 77 of a second zone 72 in the first lane 88 can be staggered in the machine direction 22 from the cross-directional centerlines 77 of the nearest adjacent second zones 72 in the second lane 88'. In the same fashion, the second zones 72 in the second lane 88' can also be staggered in the machine direction 22 from the nearest adjacent second zones 72 in the third lane 88".

Staggering of the first zone 70 in the first lane 88 in the machine direction 22 from the nearest adjacent first zones 70 in the second lane 88' provides for the different web handling characteristics of the first zones 70 from the web handling characteristics of the second zones 72 to be spread out across the modified substrate 14' in the cross-direction 23. For example, in the embodiment described herein, the first zones 70 of the modified substrate 14' can include a greater open area than the second zones 72 of the modified substrate 14'. By having a greater open area in the first zone 70 as compared to the second zone 72, the modified substrate 14' can possess different handling characteristics in the first zones 70 as compared to the second zones 72. The machine directional staggering of the first zones 70 in adjacent lanes 88, 88' helps balance the substrate handling characteristics of the modified substrate 14' across the cross-direction 23, such as by reducing curling of the modified substrate 14'. As noted above, the machine directional staggering of the first zones 70 in the first lane 88 from the first zones 70 in the second lane 88' can provide similar advantages in handling of the modified substrate 14' for other embodiments where the first zone 70 has other characteristics that differ from the second zone 72 that relate to web handling other than open area, such as basis weight, density, tensile strength, bulk thickness, surface texture, and/or urine wicking properties, among other characteristics.

The staggering of the first zones 70 in the first lane 88 from the nearest adjacent first zones 70 in the second lane 88' in the machine direction 22 for the modified substrate 14' are a result of the configuration and orientation of the first pattern lane 48 and the second pattern lane 48' in the pattern surface 34 that form the modified substrate 14'. For example, referring back to FIG. 2 shows that the first pattern zone 50 in the first pattern lane 48 has a cross-directional centerline 53 that is off-set in the longitudinal direction 57 of the pattern surface 34 (which corresponds to the machine direction 22) from the cross-directional centerlines 53 of the nearest adjacent first pattern zones 50 in the second pattern lane 48'. As discussed above with respect to the modified substrate 14' and FIG. 4, the pattern surface 34 can be configured such that the cross-directional centerlines 53 of the first pattern zones 50 of the first pattern lane 48 are disposed at a machine directional off-set of between 20%-80% of the repeating length LL of the first pattern zones 50 of the second pattern lane 48'. This same configuration of machine directional offset of the first pattern zones 50 in the second pattern lane 48' can be provided with respect to the first pattern zones 50 in the third pattern lane 48".

Additionally, the second pattern zones 52 of the first pattern lane 48 can be staggered in the longitudinal direction 57 of the pattern surface 34 (i.e., staggered in the machine direction 22) from the nearest adjacent second pattern zones 52 of the second pattern lane 48'. Also, the second pattern zones 52 of the second pattern lane 48' can be staggered in the longitudinal direction 57 of the pattern surface 34 (i.e., staggered in the machine direction 22) from the nearest adjacent second pattern zones 52 of the third pattern lane 48".

In a preferred embodiment, the pattern shell 34 can be configured such that each pattern lane 48, 48', 48" is a separate member that can be rotated with respect to one another and fixed individually to the texturing drum 36. Thus, the amount of staggering in the longitudinal direction 57 of the pattern surface 34 (which corresponds to machine direction 22) between adjacent pattern lanes 48, 48', 48" can be independently adjustable. This can provide for modification and variability of the set-up of the manufacturing of the modified substrate 14' that may vary with different codes of substrates 14 being run through the method 10 described herein.

As discussed previously with reference to FIG. 1, the modified substrate 14' can be slit into separate zoned webs 12 by a slitting device 15. Preferably, the slitting device 15 can slit the modified substrate 14' between adjacent lanes 88, 88', 88'. For example, the slitting device 15 can slit the modified substrate 14' to produce three zoned webs 12 by slitting the modified substrate 14' at the intersection between the first lane 88 and the second lane 88' and at the intersection between the second lane 88' and the third lane 88". Thus, each zoned web 12 can include a plurality of first zones 70 and second zones 72 as discussed above. Of course, it is contemplated that the modified substrate 14' can be slit into other numbers of zoned webs 12.

Slitting of the modified substrate 14' can be completed in-line on the same manufacturing line in which the modified substrate 14' is provided, or the slitting can be completed in an off-line procedure to provide separate zoned webs 12. For example, the slitting of the modified substrate 14' can be completed later as part of another manufacturing asset seeking to utilize a certain width of the modified substrate 14', and thus, one of the zoned webs 12.

After the slitting of the modified substrate 14', the zoned webs 12 can each be used for desired product applications. Registration of the first zone 70 and second zone 72 of each zoned web 12 can be completed such that each zoned web 12 can be used in the same manner without respect to the machine directional staggering of the modified substrate 14' described above.

The modified substrate 14', and resulting zoned webs 12, of the present disclosure can be comprised of various fibers. In one embodiment, the zoned webs 12 can include synthetic fibers and binder fibers. In preferred embodiments including synthetic fibers and binder fibers, the binder fibers can provide at least about 5% of the plurality of fibers by total weight of the modified substrate 14', and more preferably, at least about 10% of the plurality of fibers by total weight of the modified substrate 14'. An example of the synthetic fibers that can be used include polyester fibers, polypropylene fiber, and/or bicomponent fibers of polypropylene and polyethylene, however, it can be appreciated that other fibers may be used without departing from the scope of this disclosure. Exemplary binder fibers that can be used are ESC233 binder fibers supplied by FiberVisions, which have a linear density of 3 denier, a cut length of 40 mm, and 18 crimps per inch and ESC215 binder fibers supplied by FiberVisions, which have a linear density of 1.5 denier, a cut length of 40 mm, and 18 crimps per inch. However, it is contemplated that other types of binder fibers may be used.

In some embodiments, the zoned webs 12 can additionally or alternatively include natural fibers. The fibers can be randomly deposited and may be staple length fibers, such as those that are used, for example, in carded webs, airlaid webs, coform webs, etc., and can have a fiber length less than 100 mm, and more typically in the range of 10-60 mm. Alternatively or additionally, the fibers of the materials of the present disclosure can include more continuous fibers such as those that are found in, for example, meltblown or spunbond webs, and can have a fiber length greater than 100 mm.

Test Methods

Material Sample Analysis Test Method

The Material Sample Analysis Test Method as described herein can be used for determining the open area (also referred to as the percent open area) in a given sample of the modified substrate 14'. In this context, the percent open area is considered as the percent of an area of a material (i.e., modified substrate 14') in which light transmitted from a light source passes directly through unhindered. Generally, this image analysis method determines a numeric value of percent open area for a material via specific image analysis measurement parameters such as area. This test method and equipment also provide the ability to measure the size of an opening 76, the roundness of an opening 76, the aspect ratio for an opening 76, the two-dimensional area of a node 74, and node 74 density and spacing. This test method involves obtaining two separate digital images of the sample.

Material Apertured Zone Sample Analysis Set-Up and Determination

Figure 6:
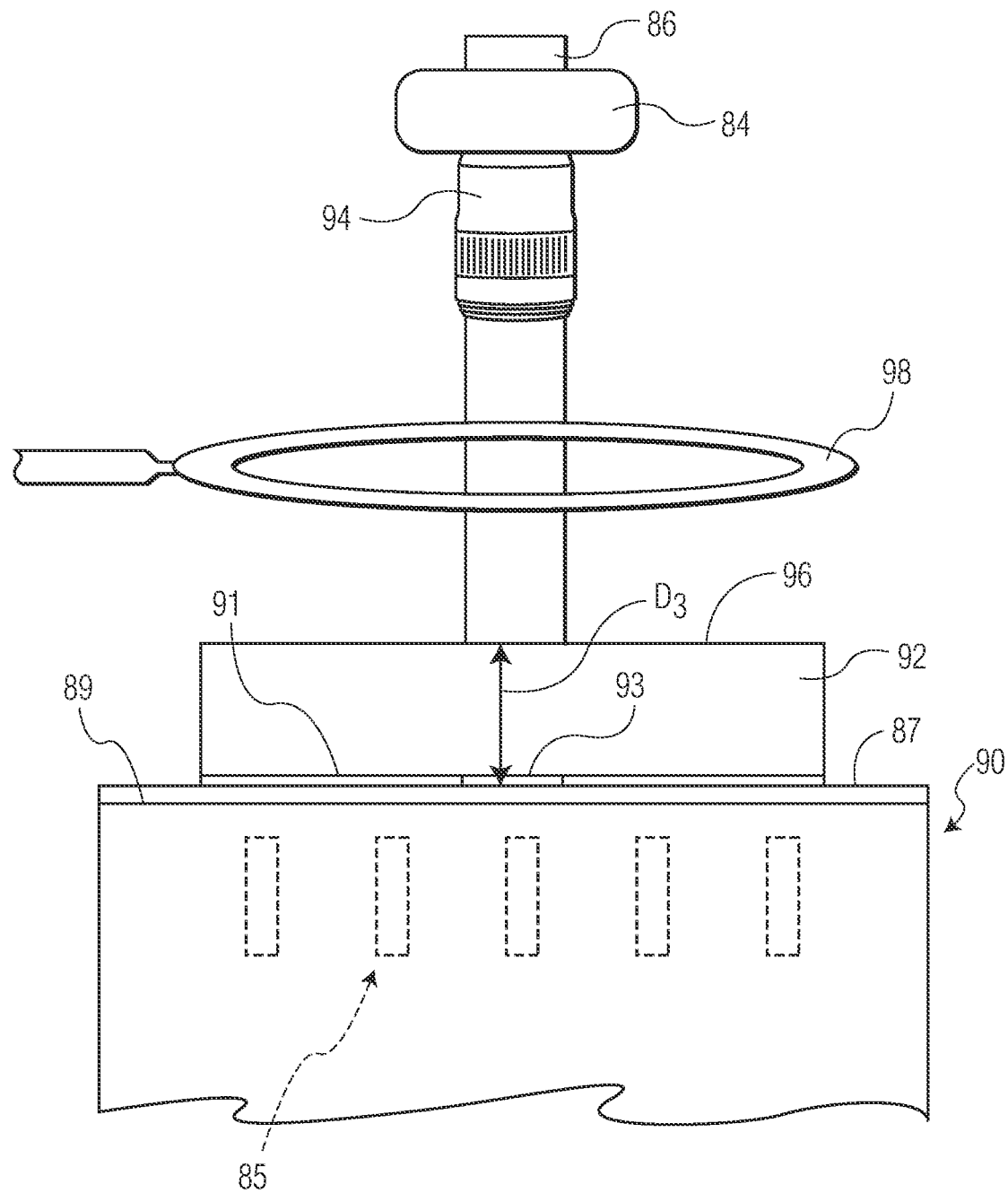
FIG. 6 is a perspective view of exemplary equipment and set-up to perform the Material Sample Analysis Test Method as described herein.

An exemplary setup for acquiring the images of the zones 70, 72 of the modified substrate 14' is representatively illustrated in FIG. 6. Specifically, a CCD video camera 84 (e.g., a Leica DFC 300 FX video camera available from Leica Microsystems of Heerbrugg, Switzerland) is mounted on a standard support 86 such as a Polaroid MP-4 Land Camera standard support formerly available from Polaroid Resource Center in Cambridge, MA, and now potentially available from a resource such as eBay. The standard support 86 is attached to a macro-viewer 90 such as a KREONITE macro-viewer available from Dunning Photo Equipment, Inc., having an office in Bixby, Oklahoma. An auto stage 92 is placed on the upper surface of the macro-viewer 90. The auto stage 92 is used to automatically move the position of a given sample for viewing by the camera. A suitable auto stage 92 is Model H112, available from Prior Scientific Inc., having an office in Rockland, MA.

The specimen (not shown in FIG. 6) is placed on the auto stage 92 of a Leica Microsystems QWIN Pro Image Analysis system, under the optical axis of a 60 mm lens 94 having an f-stop setting of 4, such as a Nikon AF Micro Nikkor, manufactured by Nikon Corporation, having an office in Tokyo, Japan. The lens 94 is attached to the camera 84 using a c-mount adaptor. The distance from the front face of the lens 94 to the sample is approximately 55 cm. The sample is laid flat on the auto stage surface 96 and any wrinkles removed by gentle stretching and/or fastening it to the auto stage surface 96 using transparent adhesive tape at its outer edges. The sample surface is illuminated with incident fluorescent lighting provided by a 16 inch diameter, 40 watt, Circline fluorescent light 98, such as that manufactured by General Electric Company, having an office in Boston, MA. The light 98 is contained in a fixture that is positioned so it is centered over the sample and is approximately 3 cm above the sample surface. The illumination level of the light 98 is controlled with a Variable Auto-transformer (not shown), type 3PN1010, available from Staco Energy Products Co. having an office in Dayton, OH. Transmitted light is also provided to the sample from beneath the auto stage by a bank of four, 2-foot, EMC, Double-End Powered LED tube lights 85 which are dimmable and available from Fulight Optoelectronic Materials, LLC. The LED lights 85 are covered with a diffusing plate 87. The diffusing plate 87 is inset into, and forms a portion of, the upper surface 89 of the macro-viewer 90. This illumination source is overlaid with black mask 91 possessing a 3-inch by 3-inch opening 93. The opening 93 is positioned so that it is centered under the optical axis of the camera 84 and lens 94 system. The distance D3 from the fluorescent light opening 93 to the surface 96 of the auto stage 92 is approximately 17 cm. The illumination level of the fluorescent light bank is also controlled with a separate power control box (not shown) configured for dimmable LED lights.

The image analysis software platform used to perform the percent open area and aperture size measurements is a QWIN Pro (Version 3.5.1) available from Leica Microsystems, having an office in Heerbrugg, Switzerland. Alternatively, LAS Macro Editor, the next generation of software following QWIN Pro, could be used to perform the analysis. The system and images are also accurately calibrated using the QWIN software and a standard ruler with metric markings at least as small as one millimeter. The calibration is performed in the horizontal dimension of the video camera image. Units of millimeters per pixel are used for the calibration.

Thus, the method for determining the percent open area and opening size of a given specimen includes the step of performing measurements on the transmitted light image. Specifically, an image analysis algorithm is used to acquire and process images as well as perform measurements using Quantimet User Interactive Programming System (QUIPS) language. The image analysis algorithm is reproduced below. For purposes of clarity, the references in the algorithm to "bumps" or "projections" refers to nodes 74 for the modified substrate 14' and the references to "open areas" or "apertures" refers to openings 76 for the modified substrate 14'.

```
DEFINE VARIABLES & OPEN FILES
    The following line designates the computer location where data is sent to
    Open File (C:\Data\94054 - Nhan (patent)\data.xls, channel #1)
    TOTCOUNT = 0
    TOTFIELDS = 0
    MFRAMEH = 875
    MFRAMEW = 1249
    SAMPLE ID AND SET UP
    Configure ( Image Store 1392 x 1040, Grey Images 81, Binaries 24 )
    Enter Results Header
    File Results Header ( channel #1 )
    File Line ( channel #1 )
    PauseText ( "Enter sample image prefix name now." )
    Input ( TITLE$ )
    PauseText ( "Set sample into position." )
```

-continued

```
  Image Setup DC Twain [PAUSE] ( Camera 1, AutoExposure Off, Gain 0.00, ExposureTime 34.23
msec, Brightness 0, Lamp 38.83 )
  Measure frame ( x 74, y 110, Width 1249, Height 875 )
  Image frame ( x 0, y 0, Width 1392, Height 1040 )
  -- Calvalue = 0.0377 mm/px
  CALVALUE = 0.0377
  Calibrate ( CALVALUE CALUNITS$ per pixel )
  FRMAREA = MFRAMEH*MFRAMEW*(CALVALUE**2)
  Clear Accepts
  For ( SAMPLE = 1 to 1, step 1 )
    Clear Accepts
    File ( "Field No.", channel #1, field width: 9, left justified )
    File ( "% Open Area", channel #1, field width: 7, left justified )
    File ( "Bump Density", channel #1, field width: 13, left justified )
    File ( "Bump Spacing", channel #1, field width: 15, left justified )
    File Line ( channel #1 )
    Stage ( Define Origin )
    Stage ( Scan Pattern, 1 x 5 fields, size 82500.000000 x 39000.000000 )
    IMAGE ACQUISITION I - Projection isolation
    For ( FIELD = 1 to 5, step 1 )
      Measure frame ( x 74, y 110, Width 1249, Height 875 )
      Display ( Image0 (on), frames (on,on), planes (off,off,off,off,off,off), lut 0, x 0, y 0, z 1, Reduction
off )
      PauseText ( "Ensure incident lighting is correct (WL = 0.88 – 0.94) and acquire image." )
      Image Setup DC Twain [PAUSE] ( Camera 1, AutoExposure Off, Gain 0.00, ExposureTime 34.23
msec, Brightness 0, Lamp 38.83 )
      Acquire ( into Image0 )
      DETECT - Projections only
      PauseText ( "Ensure that threshold is set at least to the right of the left gray-level histogram peak
which corresponds to the 'land' region." )
      Detect [PAUSE] ( whiter than 129, from Image0 into Binary0 delineated )
      BINARY IMAGE PROCESSING
      Binary Amend ( Close from Binary0 to Binary1, cycles 10, operator Disc, edge erode on )
      Binary Identify ( FillHoles from Binary1 to Binary1 )
      Binary Amend ( Open from Binary1 to Binary2, cycles 20, operator Disc, edge erode on )
      Binary Amend ( Close from Binary2 to Binary3, cycles 8, operator Disc, edge erode on )
      PauseText ( "Toggle <control> and <b> keys to check projection detection and correct if
necessary." )
      Binary Edit [PAUSE] ( Reject from Binary3 to Binary3, nib Fill, width 2 )
      Binary Logical ( copy Binary3, inverted to Binary4 )
      IMAGE ACQUISITION 2 - % Open Area & Aperture Size
      Measure frame ( x 74, y 110, Width 1249, Height 875 )
      Display ( Image0 (on), frames (on,on), planes (off,off,off,off,off,off), lut 0, x 0, y 0, z 1, Reduction
off )
      PauseText ( "Turn off incident light & ensure transmitted lighting is correct (WL = 0.95) and
acquire image." )
      Image Setup DC Twain [PAUSE] ( Camera 1, AutoExposure Off, Gain 0.00, ExposureTime 34.23
msec, Brightness 0, Lamp 38.83 )
      Acquire ( into Image0 )
      ACQFILE$ = "C:\Images\94054 - Nhan\"+TITLE$+"_"+STR$(FIELD)+".jpg"
      Write image ( from ACQOUTPUT into file ACQFILE$ )
      DETECT - Open areas only
      Detect ( whiter than 127, from Image0 into Binary10 delineated )
      BINARY IMAGE PROCESSING
      Binary Amend ( Close from Binary10 to Binary11, cycles 5, operator Disc, edge erode on )
      Binary Identify ( FillHoles from Binary11 to Binary12 )
      Binary Amend ( Open from Binary12 to Binary13, cycles 10, operator Disc, edge erode on )
      Binary Identify ( EdgeFeat from Binary13 to Binary14 )
      PauseText ( "Ensure apertures are detected accurately." )
      Binary Edit [PAUSE] ( Reject from Binary14 to Binary14, nib Fill, width 2 )
      FIELD MEASUREMENTS - % Open Area, Bump Density & Spacing
        -- % open area
      MFLDIMAGE = 10
      Measure field ( plane MFLDIMAGE, into FLDRESULTS(1), statistics into FLDSTATS(7,1) )
        Selected parameters: Area%
      Field Histogram #1 ( Y Param Number, X Param Area%, from 0. to 60., linear, 20 bins )
      PERCOPENAREA = FLDRESULTS(1)
      -- bump density & spacing
      MFLDIMAGE = 3
      Measure field ( plane MFLDIMAGE, into FLDRESULTS(5), statistics into FLDSTATS(7,5) )
        Selected parameters: Area, Intercept H, Intercept V, Area%,
        Count/Area
      BUMPDENSITY = FLDRESULTS(5)
      MNSPACE1 = (FRMAREA−FLDRESULTS(1))/(FLDRESULTS(2)+FLDRESULTS(3))/2
      Field Histogram #2 ( Y Param Number, X Param MNSPACE1, from 0. to 50., linear, 25 bins )
      File ( FIELD, channel #1, 0 digits after '.' )
      File ( PERCOPENAREA, channel #1, 1 digit after '.' )
```

```
    File ( BUMPDENSITY, channel #1, 1 digit after '.' )
    File ( MNSPACE1, channel #1, 1 digit after '.' )
    File Line ( channel #1 )
    FEATURE MEASUREMENTS - Aperture and bump sizes
    -- Bump Size
    Measure feature ( plane Binary3, 8 ferets, minimum area: 24, grey image: Image0 )
       Selected parameters: Area, X FCP, Y FCP, EquivDiam
    Feature Histogram #1 ( Y Param Number, X Param Area, from 1. to 100., logarithmic, 20 bins )
    Feature Histogram #2 ( Y Param Number, X Param EquivDiam, from 1. to 100., logarithmic, 20
bins )
    -- Aperture Size
    Measure feature ( plane Binary14, 8 ferets, minimum area: 24, grey image: Image0 )
       Selected parameters: Area, X FCP, Y FCP, Roundness, AspectRatio,
       EquivDiam
    Feature Histogram #3 ( Y Param Number, X Param Area, from 1. to 100., logarithmic, 20 bins )
    Feature Histogram #4 ( Y Param Number, X Param EquivDiam, from 1. to 100., logarithmic, 20
bins )
    Feature Histogram #5 ( Y Param Number, X Param Roundness, from 0.8999999762 to
2.900000095, linear, 20 bins )
    Feature Histogram #6 ( Y Param Number, X Param AspectRatio, from 1. to 3., linear, 20 bins )
    Stage ( Step, Wait until stopped + 1100 msecs )
    Next ( FIELD )
  Next ( SAMPLE )
  File Line ( channel #1 )
  File Line ( channel #1 )
  OUTPUT FEATURE HISTOGRAMS
  File ( "Bump Size (area - sq. mm)", channel #1 )
  File Line ( channel #1 )
  File Feature Histogram Results ( #1, differential, statistics, bin details, channel #1 )
  File Line ( channel #1 )
  File Line ( channel #1 )
  File ( "Bump Size (ECD - mm)", channel #1 )
  File Line ( channel #1 )
  File Feature Histogram Results ( #2, differential, statistics, bin details, channel #1 )
  File Line ( channel #1 )
  File Line ( channel #1 )
  File ( "Aperture Size (area - sq. mm)", channel #1 )
  File Line ( channel #1 )
  File Feature Histogram Results ( #3, differential, statistics, bin details, channel #1 )
  File Line ( channel #1 )
  File Line ( channel #1 )
  File ( "Aperture Size (ECD - mm)", channel #1 )
  File Line ( channel #1 )
  File Feature Histogram Results ( #4, differential, statistics, bin details, channel #1 )
  File Line ( channel #1 )
  File Line ( channel #1 )
  File ( "Aperture Roundness", channel #1 )
  File Line ( channel #1 )
  File Feature Histogram Results ( #5, differential, statistics, bin details, channel #1 )
  File Line ( channel #1 )
  File Line ( channel #1 )
  File ( "Aperture Aspect Ratio", channel #1 )
  File Line ( channel #1 )
  File Feature Histogram Results ( #6, differential, statistics, bin details, channel #1 )
  File Line ( channel #1 )
File Line ( channel #1 )
Close File ( channel #1 )
END
```

The QUIPS algorithm is executed using the QWIN Pro software platform. The analyst is initially prompted to enter the specimen set information which is sent to the EXCEL file.

The analyst then enters an image file prefix name corresponding to the specimen identification. This will be used by the algorithm to save images acquired during the analysis to a specified file location. The analyst is next prompted by a live image set up window on the computer monitor screen to place a specimen onto the auto-stage. The sample should be laid flat and gentle force applied at its edges to remove any macro-wrinkles that may be present. At this time, the Circline fluorescent light 98 can be on to assist in positioning the specimen. Next, the analyst is prompted to adjust the incident Circline fluorescent incident light 98 via the Variable Auto-transformer to a white level reading of approximately 0.9. The sub-stage transmitted light should either be turned off at this time or masked using a piece of light-blocking, black construction paper placed over the 3 inch by 3 inch opening 93.

The analyst is now prompted to ensure that the detection threshold is set to the proper level for detection of the nodes 74 using the Detection window which is displayed on the computer monitor screen. Typically, the threshold is set using the white mode at a point approximately near the middle of the 8-bit gray-level range (e.g. 127). If necessary, the threshold level can be adjusted up or down so that the resulting detected binary will optimally encompass the nodes 74 shown in the acquired image.

After the algorithm automatically performs several binary image processing steps on the detected binary of the nodes 74, the analyst will be given an opportunity to re-check node detection and correct any inaccuracies. The analyst can toggle both the 'control' and 'b' keys simultaneously to re-check node detection against the underlying acquired gray-scale image. If necessary, the analyst can select from a set of binary editing tools (e.g. draw, reject, etc.) to make any minor adjustments. If care is taken to ensure proper illumination and detection in the previously described steps, little or no correction at this point should be necessary.

Next, the analyst is prompted to turn off the incident Circline fluorescent light 98 and either turn on the sub-stage transmitted light or remove the light blocking mask. The sub-stage transmitted light is adjusted by the LED power controller to a white level reading of approximately 0.95. At this point, the image focus can be optimized for the specific zone of the modified substrate 14' including openings 76.

The algorithm, after performing additional operations on the resulting separate binary images for openings 76, will then prompt the analyst to re-check opening 76 detection against the underlying gray-scale image. If necessary, the analyst can select from a set of binary editing tools (e.g. draw, reject, etc.) to make any minor adjustments.

The algorithm will then automatically perform measurements and output the data into a designated EXCEL spreadsheet file.

Following the transfer of data, the algorithm will direct the auto-stage to move to the next field-of-view and the process of turning on the incident, Circline fluorescent light 98 and blocking the transmitted sub-stage lighting will begin again. This process will repeat four times so that there will be five sets of data from five separate field-of-view images per single sampling replicate.

After completion of the analysis, the following measurement parameter data will be located in the EXCEL file after measurements and data transfer has occurred:

Percent Open Area
Node Density (No. per sq. metre)
Node Spacing (mm)
Node Size (One histogram for area in $mm^2$ and one histogram for equivalent circular diameter in mm)
Aperture Size (One histogram for area in $mm^2$ and one histogram for equivalent circular diameter in mm)
Aperture Roundness
Aperture Aspect Ratio The final specimen mean spread value is usually based on an N=5 analysis from five, separate, specimen subsample replicates. A comparison of the percent open area, opening 76 (aperture) size and other parameters acquired by the algorithm between different specimens can be performed using a Student's T analysis at the 90% confidence level.

Material Side Zone Percent Open Area Set-Up and Determination

The setup for acquiring the images of the material side zones 80a, 80b, 82a, 82b is similar to the set-up for acquiring images of modified substrate 14' in the first zone 70 or second zone 72 with a few minor differences, as detailed below. This methodology can also be used for determining the open area for the transition zones 73 of the modified substrate 14'.

The camera and lens, the support, and the stage used to capture the images of the material side zones, and settings for the same, are all the same as used in the Material Apertured Zone Sample Analysis Set-up and Determination. However, in the present set-up, no macro-viewer was used. The test material side zone sample is prepared and placed onto the auto-stage surface 96 as in the Material Apertured Zone Sample Analysis Set-up and Determination. However, instead of illuminating the sample surface with incident fluorescent lighting provided by a Circline fluorescent light, light was transmitted to the sample from under the sample by a ChromaPro 45 device, formerly available from Circle S in Tempe, AZ, that had a 3-inch by 3-inch sized opening black mask overlaid on its surface.

As with the Material Apertured Zone Sample Analysis Set-up and Determination, the image analysis software platform used to perform the percent open area measurement for the material side zones is the QWIN Pro (Version 3.5.1) available from Leica Microsystems. Alternatively, LAS Macro Editor, the next generation of software following QWIN Pro, could be used to perform the analysis. The system and images are also accurately calibrated using the QWIN software and a standard ruler with metric markings at least as small as one millimeter. The calibration is performed in the horizontal dimension of the video camera image. Units of millimeters per pixel are used for the calibration.

In the Material Side Zone Percent Open Area Set-up and Determination, upon running the QWIN Pro program, the light level was set at 0.95 using the white level function in the QWIN Pro program to adjust the light output of the ChromaPro light output. The QWIN Pro program was further configured to move the Prior auto-stage so that six images were automatically acquired and measured from each side of the sample material, resulting in twelve total measurements.

Thus, the method for determining the percent open area of a side zone includes the step of performing measurements on the transmitted light image. Specifically, an image analysis algorithm is used to acquire and process images as well as perform measurements using Quantimet User Interactive Programming System (QUIPS) language. The image analysis algorithm is reproduced below.

```
DEFINE VARIABLES & OPEN FILES
The following line designates the computer location where data is sent to
Open File ( D:\Data\103470 - Nhan\data.xls, channel #1 )
    TOTCOUNT = 0
    TOTFIELDS = 0
    MFRAMEH = 875
    MFRAMEW = 1249
    SAMPLE ID AND SET UP
    Configure ( Image Store 1392 x 1040, Grey Images 81, Binaries 24 )
    Enter Results Header
    File Results Header ( channel #1 )
    File Line ( channel #1 )
    PauseText ( "Enter sample image prefix name now." )
    Input ( TITLE$ )
    Measure frame ( x 511, y 50, Width 446, Height 940 )
    Image frame ( x 0, y 0, Width 1392, Height 1040 )
    PauseText ( "Set sample into position." )
```

```
   Image Setup DC Twain [PAUSE] ( Camera 1, AutoExposure Off, Gain 0.00, ExposureTime 34.23
msec, Brightness 0, Lamp 38.83 )
   -- Calvalue = 0.0333 mm/px
   CALVALUE = 0.0333
   Calibrate ( CALVALUE CALUNITS$ per pixel )
   FRMAREA = MFRAMEH*MFRAMEW*(CALVALUE**2)
   File ( "Field No.", channel #1, field width: 9, left justified )
   File ( "% Open Area", channel #1, field width: 7, left justified )
   File Line ( channel #1 )
   For ( SAMPLE = 1 to 2, step 1 )
      Clear Accepts
      Stage ( Define Origin )
      Stage ( Scan Pattern, 1 x 6 fields, size 82500.000000 x 39000.000000 )
      For ( FIELD = 1 to FIELDS, step 1 )
         IMAGE ACQUISITION
         ACQOUTPUT = 0
         Measure frame ( x 511, y 50, Width 446, Height 940 )
         Display ( Image0 (on), frames (on,on), planes (off,off,off,off,off,off), lut 0, x 0, y 0, z 1, Reduction
off )
         PauseText ( "Turn off incident light & ensure transmitted lighting is correct (WL = 0.95) and
acquire image." )
         Image Setup DC Twain [PAUSE] ( Camera 1, AutoExposure Off, Gain 0.00, ExposureTime 34.23
msec, Brightness 0, Lamp 38.83 )
         Acquire ( into Image0 )
         ACQFILES = "D:\Images\103470 - Nhan\"+TITLE$+"_"+STR$(FIELD)+".jpg"
         Write image ( from ACQOUTPUT into file ACQFILE$ )
         DETECT - Open areas only
         Detect ( whiter than 164, from Image0 into Binary10 )
         BINARY IMAGE PROCESSING
         Binary Amend ( Close from Binary10 to Binary11, cycles 1, operator Disc, edge erode on )
         Binary Identify ( FillHoles from Binary11 to Binary12 )
         Binary Identify ( EdgeFeat from Binary12 to Binary13 )
         FIELD MEASUREMENTS
         -- % open area
         MFLDIMAGE = 13
         Measure field ( plane MFLDIMAGE, into FLDRESULTS(1), statistics into FLDSTATS(7,1) )
            Selected parameters: Area%
         Field Histogram #1 ( Y Param Number, X Param Area%, from 0. to 5., linear, 20 bins )
         Display Field Histogram Results ( #1, horizontal, differential, bins + graph (Y axis linear), statistics
)
         Data Window ( 1449, 599, 423, 270 )
         PERCOPENAREA = FLDRESULTS(1)
         File ( FIELD, channel #1, 0 digits after '.' )
         File ( PERCOPENAREA, channel #1, 1 digit after '.' )
         File Line ( channel #1 )
         FEATURE MEASUREMENTS
         -- Aperture Size
         Stage ( Step, Wait until stopped + 1100 msecs )
      Next ( FIELD )
      File Line ( channel #1 )
      PauseText ( "Load next replicate now." )
      Image Setup DC Twain [PAUSE] ( Camera 1, AutoExposure Off, Gain 0.00, ExposureTime 23.16
msec, Brightness 0, Lamp 38.83 )
   Next ( SAMPLE )
   File Line ( channel #1 )
   OUTPUT FEATURE HISTOGRAMS
   File ( "% Area Histogram", channel #1 )
   File Line ( channel #1 )
   File Line ( channel #1 )
   File Field Histogram Results ( #1, differential, statistics, bin details, channel #1 )
   Close File ( channel #1 )
END
```

In the Material Side Zone Percent Open Area Set-up and Determination, the QUIPS algorithm is executed using the QWIN Pro software platform. The analyst is initially prompted to enter the specimen set information which is sent to the EXCEL file.

The analyst then enters an image file prefix name corresponding to the specimen identification. This will be used by the algorithm to save images acquired during the analysis to a specified file location. The analyst is next prompted by a live image set up window on the computer monitor screen to place a specimen onto the auto-stage. The sample should be laid flat and gentle force applied at its edges to remove any macro-wrinkles that may be present. At this point, the light level should be set at 0.95 using the white level function in the QWIN Pro program to adjust the light output of the ChromaPro light output, if not already done so. At this point, the image focus can be optimized for the side zone 80a, 80b, 82a, 82b, or the transition zones 73, of the modified substrate 14'.

The algorithm, after performing additional operations on the resulting separate binary images for micro-apertures and/or regions of greatly reduced fiber density in the side zones 80a, 80b, 82a, 82b, or transition zones 73 will then prompt the analyst to re-check detection of the micro-apertures and/or regions of greatly reduced fiber density against the underlying gray-scale image. If necessary, the analyst can select from a set of binary editing tools (e.g. draw, reject, etc.) to make any minor adjustments.

The algorithm will then automatically perform measurements and output the data into a designated EXCEL spreadsheet file.

Following the transfer of data, the algorithm will direct the auto-stage to move to the next field-of-view. This process will repeat six times along each edge of the material side zone sample so that there will be twelve sets of data from twelve separate field-of-view images per single sampling replicate.

After completion of the analysis, the following measurement parameter data will be located in the EXCEL file after measurements and data transfer has occurred:

Percent Open Area

The final specimen mean spread value is usually based on an N=5 analysis from five, separate, specimen subsample replicates. A comparison of the percent open area acquired by the algorithm between different specimens can be performed using a Student's T analysis at the 90% confidence level.

Embodiments

Embodiment 1: A method of manufacturing zoned webs, the method comprising: providing a substrate; transferring the substrate in a machine direction; modifying the substrate to include a plurality of lanes to provide a modified substrate, the plurality of lanes comprising a first lane and a second lane, the first lane comprising a first zone and a second zone, the first zone comprising an open area greater than an open area of the second zone, the second lane comprising a third zone and a fourth zone, the third zone comprising an open area greater than an open area of the fourth zone, the first lane and the second lane being formed such that the first zone in the first lane is staggered in the machine direction from the third zone in the second lane; transferring the modified substrate; and slitting the modified substrate between adjacent lanes in the plurality of lanes to provide zoned webs, the zoned webs comprising a first zoned web comprising the first lane and a second zoned web comprising the second lane.

Embodiment 2: The method of embodiment 1, wherein the first zone in the first lane is configured the same as the third zone in the second lane and wherein the second zone in the first lane is configured the same as the fourth zone in the second lane.

Embodiment 3: The method of any embodiment 1 or 2, wherein the first lane comprises a plurality of first zones and a plurality of second zones, the plurality of first zones and the plurality of second zones being configured in an alternating fashion such that each first zone is adjacent to two second zones and each second zone is adjacent to two first zones.

Embodiment 4: The method of embodiment 3, wherein the second lane comprises a plurality of third zones and a plurality of fourth zones, the plurality of third zones and the plurality of fourth zones being configured in an alternating fashion such that each third zone is adjacent to two fourth zones and each fourth zone is adjacent to two third zones.

Embodiment 5: The method of embodiment 4, wherein the plurality of first zones in the first lane are staggered in the machine direction from the plurality of third zones in the second lane.

Embodiment 6: The method of embodiment 4, wherein a distance in the machine direction between successive third zones in the second lane provides a repeating length, and wherein each first zone in the first lane is staggered in the machine direction from nearest adjacent third zones in the second lane such that a cross-directional centerline of each first zone in the first lane is disposed at a machine direction off-set to the cross-directional centerlines of the nearest adjacent third zones in the second lane such by being between 20%-80% of the repeating length of the third zones.

Embodiment 7: The method of any one of the preceding embodiments, wherein the plurality of lanes are configured to include a plurality of first lanes alternating with a plurality of second lanes.

Embodiment 8: The method of any one of the preceding embodiments, wherein the open area of the first zone and the open area of the third zone each comprise openings in the modified substrate.

Embodiment 9: The method of any one of the preceding embodiments, wherein the first lane further comprises a first transition zone between the first zone and the second zone, the open area of the first zone being greater than an open area of the first transition zone, and wherein the second lane further comprises a second transition zone between the third zone and the fourth zone, the open area of the third zone being greater than an open area of the second transition zone.

Embodiment 10: The method of embodiment 9, wherein the open area of the first transition zone is less than an open area of the second zone.

Embodiment 11: The method of any one of the preceding embodiments, wherein modifying the substrate to include a plurality of lanes to provide a modified substrate comprises fluid entangling the substrate with fluid entanglement jets to form the first zone and the second zone in the first lane and the third zone and the fourth zone in the second lane.

Embodiment 12: The method of any one of the preceding embodiments, wherein the substrate is a nonwoven web.

Embodiment 13: A method of manufacturing zoned webs, the method comprising: providing a nonwoven substrate; transferring the substrate in a machine direction to a fluid entanglement apparatus, the fluid entanglement apparatus including a pattern surface and a plurality of fluid entanglement jets, the pattern surface comprising: a plurality of pattern lanes, the plurality of pattern lanes comprising a first pattern lane and a second pattern lane, the first pattern lane comprising a first pattern zone and a second pattern zone, the first pattern zone comprising a first plurality of projections, the second pattern lane comprising a third pattern zone and a fourth pattern zone, the third pattern zone comprising a third plurality of projections, the third pattern zone and the fourth pattern zone being formed such that the first pattern zone in the first pattern lane is staggered in the machine direction from the third pattern zone in the second pattern lane; fluid entangling the substrate with the fluid entanglement jets over the pattern surface to provide a modified substrate comprising a plurality of lanes comprising a first lane and a second lane; transferring the modified substrate; and slitting the modified substrate between adjacent lanes in the plurality of lanes to provide zoned webs, the zoned webs comprising a first zoned web comprising the first lane and a second zoned web comprising the second lane.

Embodiment 14: The method of embodiment 13, wherein fluid entangling the substrate with the fluid entanglement jets over the pattern surface to provide a modified substrate comprising a plurality of lanes comprises forming the plurality of lanes such that the first lane of the modified substrate comprises a first zone and a second zone, the first zone comprising an open area greater than an open area of the second zone, and wherein the second lane of the modified substrate comprises a third zone and a fourth zone, the third zone comprising an open area greater than an open area of the fourth zone, the first lane and the second lane being formed on the modified substrate such that the first zone in the first lane is staggered in the machine direction from the third zone in the second lane.

Embodiment 15: The method of embodiment 13 or 14, wherein the second pattern zone and the fourth pattern zone of the pattern roll do not comprise any projections.

Embodiment 16: The method of any one of embodiments 13-15, wherein the second pattern zone comprises a second plurality of projections and the fourth pattern zone comprises a fourth plurality of projections.

Embodiment 17: The method of any one of embodiments 13-16, wherein the first pattern zone in the first pattern lane is configured the same as the third pattern zone in the second pattern lane and wherein the second pattern zone in the first pattern lane is configured the same as the fourth pattern zone in the second pattern lane.

Embodiment 18: The method of any one of embodiments 13-17, wherein the first pattern lane comprises a plurality of first pattern zones and a plurality of second pattern zones, the plurality of first pattern zones and the plurality of second pattern zones being configured in an alternating fashion such that each first pattern zone is adjacent two second pattern zones and each second pattern zone is adjacent two first pattern zones, and wherein the second lane comprises a plurality of third zones and a plurality of fourth zones, the plurality of third zones and the plurality of fourth zones being configured in an alternating fashion such that each third zone is adjacent to two fourth zones and each fourth zone is adjacent to two third zones.

Embodiment 19: The method of embodiment 17, wherein a distance in the machine direction between successive third pattern zones in the second pattern lane provides a repeating length, and wherein each first pattern zone in the first pattern lane is staggered in the machine direction from nearest adjacent third pattern zones in the second pattern lane such that a cross-directional centerline of each first pattern zone in the first pattern lane is located at a machine direction off-set to the cross-directional centerlines of the nearest adjacent third pattern zones in the second pattern lane by being between 20%-80% of the repeating length of the third pattern zones.

Embodiment 20: A method of manufacturing zoned webs, the method comprising: providing a substrate; transferring the substrate in a machine direction; modifying the substrate to include a plurality of lanes to provide a modified substrate, the plurality of lanes comprising: a first lane comprising a first zone and a second zone, the first zone comprising a first substrate characteristic, the second zone comprising a second substrate characteristic, the first substrate characteristic and the second substrate characteristic providing different substrate handling characteristics between the first zone and the second zone; and a second lane comprising a third zone and a fourth zone, the third zone comprising a third substrate characteristic, the fourth zone comprising a fourth substrate characteristic, the third substrate characteristic and the fourth substrate characteristic providing different substrate handling characteristics between the third zone and the fourth zone; wherein the substrate is modified such that the first lane and the second lane are configured such that the first zone in the first lane is staggered in the machine direction from the third zone in the second lane; transferring the modified substrate; and slitting the modified substrate between adjacent lanes in the plurality of lanes to provide zoned webs, the zoned webs comprising a first zoned web comprising the first lane and a second zoned web comprising the second lane.

What is claimed is:

1. A method of manufacturing zoned webs, the method comprising:
    providing a substrate;
    transferring the substrate in a machine direction;
    modifying the substrate to include a plurality of lanes to provide a modified substrate, the plurality of lanes comprising a first lane and a second lane, the first lane comprising a first zone and a second zone, the first zone comprising an open area greater than an open area of the second zone, the second lane comprising a third zone and a fourth zone, the third zone comprising an open area greater than an open area of the fourth zone, the first lane and the second lane being formed such that the first zone in the first lane is staggered in the machine direction from the third zone in the second lane,
        wherein the first lane comprises a plurality of first zones and a plurality of second zones, the plurality of first zones and the plurality of second zones being configured in an alternating fashion such that each first zone is adjacent to two second zones and each second zone is adjacent to two first zones;
        wherein the second lane comprises a plurality of third zones and a plurality of fourth zones, the plurality of third zones and the plurality of fourth zones being configured in an alternating fashion such that each third zone is adjacent to two fourth zones and each fourth zone is adjacent to two third zones;
        wherein a distance in the machine direction between successive third zones in the second lane provides a repeating length, and wherein each first zone in the first lane is staggered in the machine direction from nearest adjacent third zones in the second lane such that a cross-directional centerline of each first zone in the first lane is disposed at a machine direction off-set to the cross-directional centerlines of the nearest adjacent third zones in the second lane such by being between 20%-80% of the repeating length of the third zones;
    transferring the modified substrate; and
    slitting the modified substrate between adjacent lanes in the plurality of lanes to provide zoned webs, the zoned webs comprising a first zoned web comprising the first lane and a second zoned web comprising the second lane.

2. The method of claim 1, wherein the first zone in the first lane is configured the same as the third zone in the second lane and wherein the second zone in the first lane is configured the same as the fourth zone in the second lane.

3. The method of claim 1, wherein the plurality of first zones in the first lane are staggered in the machine direction from the plurality of third zones in the second lane.

4. The method of claim 1, wherein the plurality of lanes are configured to include a plurality of first lanes alternating with a plurality of second lanes.

5. The method of claim 1, wherein the open area of the first zone and the open area of the third zone each comprise openings in the modified substrate.

6. The method of claim 1, wherein the first lane further comprises a first transition zone between the first zone and the second zone, the open area of the first zone being greater than an open area of the first transition zone, and wherein the second lane further comprises a second transition zone between the third zone and the fourth zone, the open area of the third zone being greater than an open area of the second transition zone.

7. The method of claim 6, wherein the open area of the first transition zone is less than an open area of the second zone.

8. The method of claim 1, wherein modifying the substrate to include a plurality of lanes to provide a modified substrate comprises fluid entangling the substrate with fluid entanglement jets to form the first zone and the second zone in the first lane and the third zone and the fourth zone in the second lane.

9. The method of claim 1, wherein the substrate is a nonwoven web.

10. A method of manufacturing zoned webs, the method comprising:
providing a nonwoven substrate;
transferring the substrate in a machine direction to a fluid entanglement apparatus, the fluid entanglement apparatus including a pattern surface and a plurality of fluid entanglement jets, the pattern surface comprising:
a plurality of pattern lanes, the plurality of pattern lanes comprising a first pattern lane and a second pattern lane, the first pattern lane comprising a first pattern zone and a second pattern zone, the first pattern zone comprising a first plurality of projections, the second pattern lane comprising a third pattern zone and a fourth pattern zone, the third pattern zone comprising a third plurality of projections, the third pattern zone and the fourth pattern zone being formed such that the first pattern zone in the first pattern lane is staggered in the machine direction from the third pattern zone in the second pattern lane;
fluid entangling the substrate with the fluid entanglement jets over the pattern surface to provide a modified substrate comprising a plurality of lanes comprising a first lane and a second lane;
transferring the modified substrate; and
slitting the modified substrate between adjacent lanes in the plurality of lanes to provide zoned webs, the zoned webs comprising a first zoned web comprising the first lane and a second zoned web comprising the second lane.

11. The method of claim 10, wherein fluid entangling the substrate with the fluid entanglement jets over the pattern surface to provide a modified substrate comprising a plurality of lanes comprises forming the plurality of lanes such that the first lane of the modified substrate comprises a first zone and a second zone, the first zone comprising an open area greater than an open area of the second zone, and wherein the second lane of the modified substrate comprises a third zone and a fourth zone, the third zone comprising an open area greater than an open area of the fourth zone, the first lane and the second lane being formed on the modified substrate such that the first zone in the first lane is staggered in the machine direction from the third zone in the second lane.

12. The method of claim 10, wherein the second pattern zone and the fourth pattern zone of the pattern roll do not comprise any projections.

13. The method of claim 10, wherein the second pattern zone comprises a second plurality of projections and the fourth pattern zone comprises a fourth plurality of projections.

14. The method of claim 10, wherein the first pattern zone in the first pattern lane is configured the same as the third pattern zone in the second pattern lane and wherein the second pattern zone in the first pattern lane is configured the same as the fourth pattern zone in the second pattern lane.

15. The method of claim 14, wherein a distance in the machine direction between successive third pattern zones in the second pattern lane provides a repeating length, and wherein each first pattern zone in the first pattern lane is staggered in the machine direction from nearest adjacent third pattern zones in the second pattern lane such that a cross-directional centerline of each first pattern zone in the first pattern lane is located at a machine direction off-set to the cross-directional centerlines of the nearest adjacent third pattern zones in the second pattern lane by being between 20%-80% of the repeating length of the third pattern zones.

16. The method of claim 10, wherein the first pattern lane comprises a plurality of first pattern zones and a plurality of second pattern zones, the plurality of first pattern zones and the plurality of second pattern zones being configured in an alternating fashion such that each first pattern zone is adjacent two second pattern zones and each second pattern zone is adjacent two first pattern zones, and wherein the second lane comprises a plurality of third zones and a plurality of fourth zones, the plurality of third zones and the plurality of fourth zones being configured in an alternating fashion such that each third zone is adjacent to two fourth zones and each fourth zone is adjacent to two third zones.

* * * * *